(12) United States Patent
Choo et al.

(10) Patent No.: US 8,906,678 B2
(45) Date of Patent: Dec. 9, 2014

(54) USE OF MARKERS OF UNDIFFERENTIATED PLURIPOTENT STEM CELL

(75) Inventors: Boon Hwa Andre Choo, Singapore (SG); Wey Jia Fong, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 0 days.

(21) Appl. No.: 13/583,546

(22) PCT Filed: Mar. 10, 2011

(86) PCT No.: PCT/SG2011/000095
§ 371 (c)(1),
(2), (4) Date: Sep. 7, 2012

(87) PCT Pub. No.: WO2011/112155
PCT Pub. Date: Sep. 15, 2011

(65) Prior Publication Data
US 2013/0115623 A1    May 9, 2013

Related U.S. Application Data

(60) Provisional application No. 61/312,310, filed on Mar. 10, 2010.

(51) Int. Cl.
*C12N 5/07* (2010.01)
*C12N 5/00* (2006.01)
*C12N 5/071* (2010.01)
*C12N 5/0735* (2010.01)
*C07D 409/14* (2006.01)

(52) U.S. Cl.
CPC ............ *C07D 409/14* (2013.01); *C12N 5/0606* (2013.01)
USPC ............ 435/325; 435/347; 435/354; 435/366

(58) Field of Classification Search
USPC .................................. 435/325, 347, 366, 354
See application file for complete search history.

(56) References Cited

U.S. PATENT DOCUMENTS 5,942,435 A * 8/1999 Wheeler ........................ 435/325

FOREIGN PATENT DOCUMENTS

WO    WO-99/24614 A1    5/1999

OTHER PUBLICATIONS

Deb et al., (Stem Cells, Basics and Applications, 2009, Tata McGraw Hill, title and bib page and pp. 484-485). 4 pages total.*
Brevini et al., 2010, Theriogenology, vol. 74, pp. 544-550.*
Paris et al., 2010, Theriogenology, vol. 74, pp. 516-524.*
Munoz et al. (2008, Theriogenology, vol. 69, pp. 1159-1164.*
Lee et al., 2010, FEBS J., vol. 277, pp. 488-500.*
Najm et al., 2013, Med. Oncol., vol. 30, pp. 1-7.*
Jiang et al., 2013, Int. J. Clin. Exp. Pathol., vol. 6(10), pp. 2092-2101.*
Barthelery et al., 2-D DIGE Identification of Differentially Expressed Heterogeneous Nuclear Ribonucleoproteins and Transciprtion Factors During neural Differentiation of Human Embryonic Stem Cells, Proteomics Clin Appl, 2009, 3: 505-514.
Choo et al., Selection Against Undifferentiated Human Embryonic Stem Cells by a Cytotoxic Antibody Recognizing Podocalyxin-Like Protein-1, Stem Cells, 2008; 26: 1454-1463.
Drukker et al., Generation of a Monoclonal Antibody Library Against Human Embryonic Stem Cells, Methods in Molecular Biology, 2007, 407: 63-81
International Search Report and Written Opinion of PCT/SG2011/000095, 9 pages dated May 10, 2011.
Knoepfler, Deconstructing Stem Cell Tumorigenicity: A Roadmap to Safe Regenerative Medicine, Stem Cells, 2009, 27: 1050-1056.
Kolonin et al., Reversal of Obesity by Targeted Ablation of Adipose Tissue, Nature medicine, 2004, 10: 625-632.
Bhattacharya et al., A Review of Gene Expression Profiling of Human Embryonic Stem Cell Lines and Their Differentiated Progeny, Current Stem Cell Research & Therapy, 4:98-106 (2009).
Tan et al., mAb 84, a Cytotoxic Antibody that Kills Undifferentiated Human Embryonic Stem Cells via Oncosis, Stem Cells, 27:1792 (2009).
Wang et al., Prohibitin, a Potential Tumor Suppressor, Interacts with RB and Regulates E2F Function, Oncogene, 18:3501-3510 (1999).

* cited by examiner

*Primary Examiner* — Anoop Singh
*Assistant Examiner* — David A Montanari
(74) *Attorney, Agent, or Firm* — Choate Hall & Stewart, LLP; Charles E. Lyon

(57) ABSTRACT

The disclosure relates to methods of binding and identifying undifferentiated pluripotent stem cells and particularly, although not exclusively, to use of binding moieties which bind to PHB on the surface of undifferentiated pluripotent stem cells, such as PHB-binding peptides, and to methods for depleting undifferentiated stem cells from a sample.

3 Claims, 20 Drawing Sheets

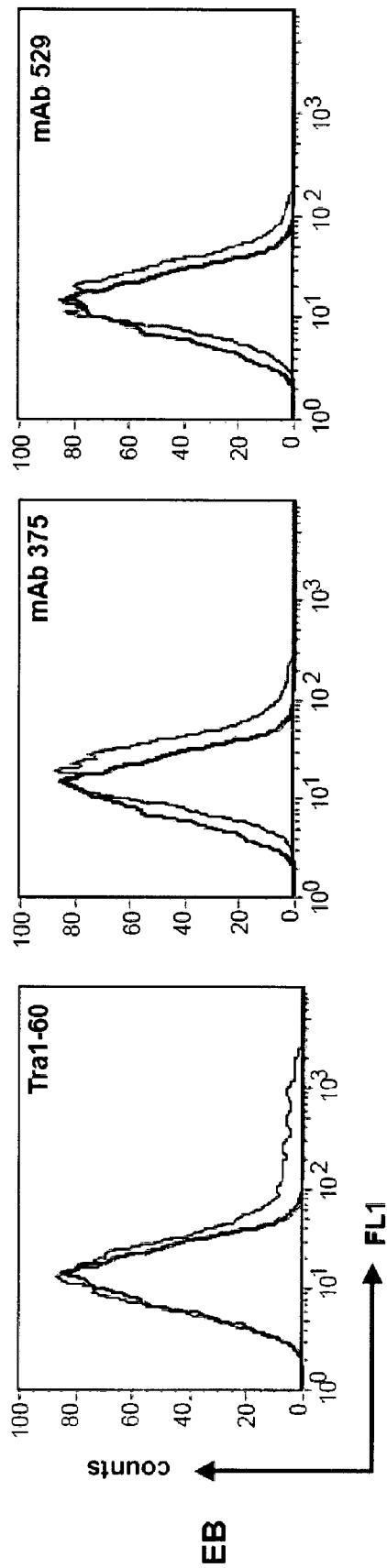
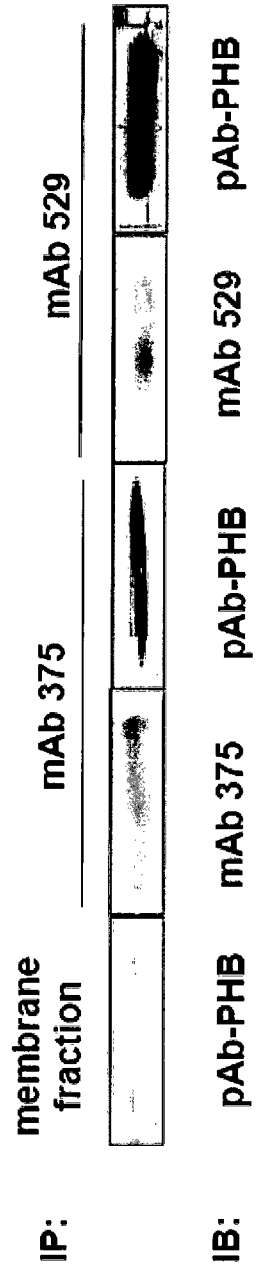
Figure 1B
Figure 1C

```
SEQUENCE LISTING

<160> NUMBER OF SEQ ID NOS: 3

<210> SEQ ID NO 1
<211> LENGTH: 9
<212> TYPE: PRT
<213> ORGANISM: Artificial sequence
<220> FEATURE:
<223> OTHER INFORMATION: Synthetic sequence: PHB-binding peptide

<400> SEQUENCE: 1

Cys Lys Gly Gly Arg Ala Lys Asp Cys
1               5

<210> SEQ ID NO 2
<211> LENGTH: 14
<212> TYPE: PRT
<213> ORGANISM: Artificial sequence
<220> FEATURE:
<223> OTHER INFORMATION: Synthetic sequence: Pro-apoptotic motif

<400> SEQUENCE: 2

Lys Leu Ala Lys Leu Ala Lys Lys Leu Ala Lys Leu Ala Lys
1               5                   10

<210> SEQ ID NO 3
<211> LENGTH: 25
<212> TYPE: PRT
<213> ORGANISM: Artificial sequence
<220> FEATURE:
<223> OTHER INFORMATION: Synthetic sequence: Pro-apoptotic PHB-binding
      peptide
```

```
<400> SEQUENCE: 3

Cys Lys Gly Gly Arg Ala Lys Asp Cys Gly Gly Lys Leu Ala Lys Leu
1               5                   10                  15

Ala Lys Lys Leu Ala Lys Leu Ala Lys
            20                  25
```

USE OF MARKERS OF UNDIFFERENTIATED PLURIPOTENT STEM CELL

PRIORITY CLAIM

This application is a national phase application under 35 USC §371 of PCT International Application No. PCT/SG2011/000095 (published PCT Application No. WO/2011/112155 A1), filed Mar. 10, 2011, which claims priority from U.S. Provisional Application No. 61/312,310 filed Mar. 10, 2010.

SEQUENCE LISTING

In accordance with 37 CFR 1.52(e)(5), a Sequence Listing in the form of a text file (entitled "Sequence_Listing.txt," created on Sep. 7, 2012, and 2 kilobytes in size) is incorporated herein by reference in its entirety.

FIELD OF THE INVENTION

The present invention relates to methods of binding and identifying undifferentiated pluripotent stem cells and particularly, although not exclusively, to use of binding moieties which bind to PHB on the surface of undifferentiated pluripotent stem cells, such as PHB-binding peptides. The invention also relates to methods for depleting undifferentiated stem cells from a sample.

BACKGROUND TO THE INVENTION

Human embryonic stem cells (hESC), first isolated from the inner cell mass of the blastocyst, possess dual capabilities of extensive self renewal and multilineage differentiation. Their proliferative capacity, together with the ability to become specialized, makes hESC suitable for use in regenerative medicine and drug discovery (1,2). However, cell surface markers routinely used for characterizing hESC are not unique as they have been used to characterize human embryonal carcinoma (EC) cells (3,4). Therefore, it is necessary to identify novel antigens, specific to hESC, for efficient evaluation of pluripotency and different stages of development during differentiation.

To achieve this, we have previously reported the generation of monoclonal antibodies (mAb) that bind specifically to undifferentiated hESC (5) and in this study, we have identified the common antigen target for two of the mAbs (mAb 375 and mAb 529) as Prohibitin (PHB).

PHB is a highly conserved protein in eukaryotic cells and is present in multiple cellular compartments such as the mitochondria (6,7), nucleus (8-10) and plasma membrane (11-13). In addition to its role as chaperone proteins in the mitochondria (6,7), PHB also modulates cell proliferation in cancer cells, when it localizes to the nucleus (8,10,14). In a detailed study on breast cancer cells by Wang et al, PHB has been reported to interact with retinoblastoma protein (Rb) and regulates E2F transcriptional activity and this regulation correlates with its growth-suppressive activity (10,15,16). Recent studies have also highlighted PHB as a surface vascular marker of adipose tissue and it can be used as an internalization receptor that may be used for targeted delivery of therapeutic compounds (11). PHB has also been shown to be indispensable for activation of ERK pathway, where direct interaction with PHB is required for C-Raf activation (13). Since Ras mutations are commonly found in tumours (17), PHB could potentially be a target for tumour therapy.

The use of embryonic stem cells in medicine is limited due to the significant ethical concerns associated with the use of embryos. Recently, the Yamanaka Lab (Takahashi et al (2007) Induction of Pluripotent Stem Cells from Adult Human Fibroblasts by Defined Factors. Cell 131(5):861-72) and Thomson Lab (Yu et al (2007) Induced Pluripotent Stem Cell Lines Derived from Human Somatic Cells. Science 318(5858):1917-20) demonstrated that human fibroblasts can be reprogrammed by the transient overexpression of a small number of genes into induced pluripotent stem cells (IPSCs) which functionally and phenotypically resemble embryonic stem cells (ESCs). Thus, pluripotent stem cells can be obtained without the need for the destruction of embryos.

Although undifferentiated stem cells may be used in cell therapy, it is considered to be beneficial to use cells which have started to differentiate, or are differentiated. Methods of encouraging stem cells to differentiate into particular cell lineages are well known in the art. Once the differentiation process has started or proceeded, it is beneficial to remove or destroy undifferentiated hESCs in a sample which may otherwise form undesirable teratomas. Teratomas typically contain a mixture of differentiated or partly differentiated cell types. Despite the potential of IPSC therapy, the problem of teratoma formation by residual IPSC after differentiation remains and needs to be addressed.

SUMMARY OF THE INVENTION

The present inventors have identified, using mAb 375 and mAb 529, that prohibitin (PHB) is a unique surface marker of undifferentiated pluripotent stem cells.

Here, PHB in hESC was observed to relocalize to the nucleus under differentiating conditions. A loss of PHB surface expression was also detected when MAPK activity was down-regulated. However, when the pathway was re-stimulated, PHB surface expression was restored; thus implying that PHB surface expression may be dependent on MAPK pathway.

An aspect of the invention therefore provides a method of binding and/or identifying an undifferentiated pluripotent stem cell or cells in a sample containing such cells, the method comprising binding a cell or cells within the sample that express prohibitin (PHB) on their surface and optionally identifying an undifferentiated pluripotent stem cell or cells in the sample.

A PHB-binding moiety may be used to bind one or more undifferentiated stem cells in a sample. For example, a PHB-binding moiety may be a peptide or antibody molecule which binds or is capable of binding to PHB on the surface of an undifferentiated pluripotent stem cell.

The present inventors evaluated the effects of a pro-apoptotic peptide, which binds to PHB localized on the cell surface. Cell death via apoptosis was observed in both hESC and IPSCs within 48 h of incubation.

Accordingly, the inventors have found that PHB-binding moieties, for example PHB-binding peptides described herein, may be used to destroy or kill cells which express PHB on their surface, such as undifferentiated pluripotent stem cells.

Furthermore, PHB-binding moieties may be useful for binding, identifying, isolating, separating, purifying, enriching, killing or removing undifferentiated pluripotent stem cells, for example from a sample or population containing differentiated and undifferentiated hESCs and/or IPSCs.

Binding moieties may also be useful for identifying, isolating, separating, purifying, or enriching differentiated pluripotent stem cells.

Preferably, a binding moiety such as a peptide described herein destroys, or is capable of destroying (i.e. killing) undifferentiated pluripotent stem cells such as undifferentiated hESCs and/or IPSCs. For example, a binding moiety which targets undifferentiated pluripotent stem cells may include a cell-killing portion, for example a cytotoxic and/or pro-apoptotic portion or domain.

Accordingly, a peptide described herein may be used to remove residual undifferentiated pluripotent stem cells from differentiating cultures before transplantation.

An aspect of the invention provides a method of binding an undifferentiated pluripotent stem cell or cells in a sample containing one or a plurality of undifferentiated pluripotent stem cells, the method comprising:
  providing a binding moiety which binds prohibitin (PHB); and
  contacting the sample with the binding moiety under conditions permitting binding of the binding moiety to PHB on the surface of an undifferentiated pluripotent stem cell.

A method of binding may further comprise identifying the undifferentiated pluripotent stem cell or cells by virtue of being bound to the binding moiety, and/or isolating the undifferentiated pluripotent stem cell or cells from the sample by separating cells bound to the binding moiety from cells not bound to the binding moiety, and/or separating the undifferentiated pluripotent stem cell or cells from pluripotent stem cells in the sample which are differentiated, or are undergoing differentiation by separating cells bound to the peptide from cells not bound to the binding moiety.

Also provided are isolated undifferentiated pluripotent stem cells obtained by methods of isolating undifferentiated pluripotent stem cells and isolated differentiated pluripotent stems cells obtained by the methods of separating the undifferentiated pluripotent stem cell or cells from the pluripotent stem cells which are differentiated, or are undergoing differentiation, which are described herein.

An aspect of the invention provides a method of enriching pluripotent stem cells that have undergone or are undergoing differentiation from a sample comprising undifferentiated pluripotent stem cells and pluripotent stem cells that have undergone or are undergoing differentiation, the method comprising:
  (i) contacting the sample with a binding moiety which binds prohibitin (PHB) under conditions permitting the binding of the binding moiety to undifferentiated pluripotent stem cells; and
  (ii) separating cells not bound to the binding moiety from cells bound to the binding moiety so as to generate a sample that is enriched in pluripotent stem cells that have undergone or are undergoing differentiation.

An aspect of the invention provides a method of preparing a composition containing cells differentiated from undifferentiated pluripotent stem cells which contains substantially no undifferentiated pluripotent stem cells, the method comprising:
  (i) providing a population of cells comprising undifferentiated pluripotent stem cells and cells differentiated from undifferentiated pluripotent stem cells;
  (ii) contacting the population with a binding moiety which binds prohibitin (PHB) under conditions permitting the binding of the binding moiety to undifferentiated pluripotent stem cells; and
  (iii) separating cells not bound to the binding moiety from cells bound to the binding moiety.

In a method described herein, the cells bound to the binding moiety may be destroyed by virtue of being bound by the binding moiety.

Accordingly, a binding moiety may include a cell-killing portion, for example, a pro-apoptotic or cytotoxic portion or domain.

A binding moiety which binds PHB may be a peptide having an amino acid sequence as set out in SEQ ID NO: 1, or a variant thereof. For example a peptide may have an amino acid, sequence sharing at least 70% sequence identity with SEQ ID NO: 1.

Pro-apoptotic peptides which bind PHB are described herein. Preferably a pro-apoptotic PHB-binding peptide has a PHB-binding portion and a pro-apoptotic portion. For example a PHB-binding portion may have the amino acid sequence as set out in SEQ ID NO: 1 or a variant thereof. A pro-apoptotic portion may have the amino acid sequence as set out in SEQ ID NO: 2 or a variant thereof. In some embodiments, a pro-apoptotic PHB-binding peptide has an amino acid sequence as set out in SEQ ID NO: 3, or a variant thereof.

A variant amino acid sequence may be, for example, a sequence sharing at least 70%, at least 75%, at least 80%, at least 85%, at least 90%, or at least 95% sequence identity with the given sequence (e.g. SEQ ID NO: 1, 2, and/or 3).

An aspect of the invention provides a method of destroying an undifferentiated pluripotent stem cells or cells in a sample containing such cells, the method comprising:
  (i) contacting the sample with a cell-killing (e.g. a pro-apoptotic or cytotoxic) binding moiety which binds prohibitin (PHB) under conditions permitting the binding of the binding moiety to undifferentiated pluripotent stem cells; and
  (ii) allowing the binding moiety to destroy the said cell.

Also provided is a sample or composition which contains cells differentiated from undifferentiated pluripotent stem cells which sample or composition contains substantially no undifferentiated pluripotent stem cells and which sample or composition is obtained by a method described herein, in particular, a method of enriching pluripotent stem cells that have undergone or are undergoing differentiation, a method of preparing a composition, or a method of destroying undifferentiated pluripotent stem cells, as described herein.

DESCRIPTION OF PREFERRED EMBODIMENTS

The invention includes the combination of the aspects and preferred features described except where such a combination is clearly impermissible or expressly avoided.

The section headings used herein are for organizational purposes only and are not to be construed as limiting the subject matter described.

Aspects and embodiments of the present invention will now be illustrated, by way of example, with reference to the accompanying figures. Further aspects and embodiments will be apparent to those skilled in the art. All documents mentioned in this text are incorporated herein by reference.

Methods

Methods according to the present invention preferably involve binding of a PHB-binding moiety to cells that express PHB on their surface.

Methods according to the present invention may comprise:
  (a) identifying undifferentiated pluripotent stem cells;
  (b) isolating undifferentiated or differentiated pluripotent stem cells;

(c) separating undifferentiated pluripotent stem cells from other cells, e.g. from differentiated pluripotent stem cells;

(d) enriching undifferentiated or differentiated pluripotent stem cells;

(e) preparing a composition of differentiated pluripotent stem cells having substantially no undifferentiated pluripotent stem cells; or (f) preparing a composition of undifferentiated pluripotent stem cells having substantially no differentiated pluripotent stem cells.

Methods according to the present invention may involve the step of contacting a sample with a binding moiety which is capable of binding to PHB (e.g. a PHB-binding peptide). This may be under conditions suitable to permit binding of the binding moiety to PHB. Such conditions are well known to those of ordinary skill in the art, for example comprising physiological pH and physiological buffer.

The following numbered paragraphs (paras.) contain statements of broad combinations of the inventive technical features herein disclosed:

1. A method of identifying an undifferentiated pluripotent stem cell or cells in a sample containing such cells, the method comprising identifying a cell or cells within the sample that express prohibitin (PHB) on their surface.

2. A method of isolating an undifferentiated pluripotent stem cell or cells from a sample containing such cells, the method comprising isolating a cell or cells within the sample that express PHB on their surface.

3. A method of removing an undifferentiated pluripotent stem cell or cells from a sample containing such cells, the method comprising removing from the sample a cell or cells that express PHB on their surface.

4. A method of destroying an undifferentiated pluripotent stem cell or cells in a sample containing such cells, the method comprising destroying the cell or cells in the sample that express PHB on their surface.

5. An undifferentiated pluripotent stem cell isolated by the method of paragraph 2.

6. An isolated undifferentiated pluripotent stem cell which expresses PHB on its surface.

7. A composition containing cells differentiated from undifferentiated pluripotent stem cells which composition contains substantially no undifferentiated pluripotent stem cells which express PHB on their surface.

8. A method of treating a patient in need of cell therapy, the method comprising administering to the patient a cell according to paragraph 5 or 6 or a composition according to paragraph 7.

9. Use of a cell according to paragraph 5 or 6 or a composition according to paragraph 7 in the manufacture of a medicament for treating a patient in need of cell therapy.

10. A method according to any one of paragraphs 1 to 3 wherein the sample is contacted with a binding moiety which binds to PHB and the said undifferentiated pluripotent stem cell or cells are identified in or isolated from or removed from the sample by virtue of being bound by the binding moiety.

11. A method according to paragraph 10 wherein the binding moiety is a peptide.

12. A method according to paragraph 4 wherein the sample is contacted with a binding moiety which binds to PHB and the said undifferentiated pluripotent stem cell or cells are destroyed by virtue of being bound by the binding moiety.

13. A method according to paragraph 12 wherein the binding moiety is a cytotoxic or pro-apoptotic peptide.

14. A method according to paragraph 11 or paragraph 13 wherein the peptide has an amino acid sequence sharing at least 70% sequence identity with SEQ ID NO: 1.

15. A method according to paragraph 11, 13 or 14 wherein the peptide has an amino acid sequence sharing at least 70% sequence identity with SEQ ID NO: 3.

16. A method of binding an undifferentiated pluripotent stem cell or cells in a sample containing one or a plurality of undifferentiated pluripotent stem cells, the method comprising:
    providing a peptide which binds prohibitin (PHB); and
    contacting the sample with the peptide under conditions permitting binding of the peptide to PHB on the surface of an undifferentiated pluripotent stem cell.

17. A method according to paragraph 16 further comprising:
    identifying the undifferentiated pluripotent stem cell or cells by virtue of being bound to the peptide.

18. The method of paragraph 16 or claim 17 further comprising:
    isolating the undifferentiated pluripotent stem cell or cells from the sample by separating cells bound to the peptide from cells not bound to the peptide.

19. The method of any one of paragraphs 16 to 18 wherein the sample contains pluripotent stem cells which are differentiated, or are undergoing differentiation, the method further comprising:
    separating the undifferentiated pluripotent stem cell or cells from the pluripotent stem cells which are differentiated, or are undergoing differentiation by separating cells bound to the peptide from cells not bound to the peptide.

20. An isolated undifferentiated pluripotent stem cell or cells obtained by the method of paragraph 18.

21. An isolated differentiated pluripotent stem cell or cells obtained by the method of paragraph 19.

22. A method of enriching pluripotent stem cells that have undergone or are undergoing differentiation from a sample comprising undifferentiated pluripotent stem cells and pluripotent stem cells that have undergone or are undergoing differentiation, the method comprising:
    (i) contacting the sample with a peptide which binds prohibitin (PHB) under conditions permitting the binding of the peptide to undifferentiated pluripotent stem cells; and
    (ii) separating cells not bound to the peptide from cells bound to the peptide so as to generate a sample that is enriched in pluripotent stem cells that have undergone or are undergoing differentiation 23. A method of preparing a composition containing cells differentiated from undifferentiated pluripotent stem cells which contains substantially no undifferentiated pluripotent stem cells, the method comprising:
    (i) providing a population of cells comprising undifferentiated pluripotent stem cells and cells differentiated from undifferentiated pluripotent stem cells;
    (ii) contacting the population with a peptide which binds prohibitin (PHB) under conditions permitting the binding of the peptide to undifferentiated pluripotent stem cells; and
    (iii) separating cells not bound to the peptide from cells bound to the peptide.

24. A method according to paragraph 22 or paragraph 23 wherein the cells bound to the peptide are destroyed by virtue of being bound by the peptide.

25. A method according to paragraph 24 wherein the peptide is a pro-apoptotic peptide.

26. A composition containing cells differentiated from undifferentiated pluripotent stem cells which composition contains substantially no undifferentiated pluripotent stem cells which composition is obtained by the method of paragraph 23 or 24.

27. A method of destroying an undifferentiated pluripotent stem cell or cells in a sample containing such cells, the method comprising:
 (i) contacting the sample with a pro-apoptotic peptide which binds prohibitin (PHB) under conditions permitting the binding of the peptide to undifferentiated pluripotent stem cells; and
 (ii) allowing the peptide to destroy the said cell.

28. A method, an isolated pluripotent stem cell, or a composition according to any one of paragraphs 16 to 27 wherein the peptide has an amino acid sequence sharing at least 70% sequence identity with SEQ ID NO: 1.

29. A method or composition according to any one of paragraphs 24 to 27 wherein the peptide has an amino acid sequence sharing at least 70% sequence identity with SEQ ID NO: 3.

BRIEF DESCRIPTION OF THE FIGURES

Embodiments and experiments illustrating the principles of the invention will now be discussed with reference to the accompanying figures in which.

SEQUENCES

Figure 1A:
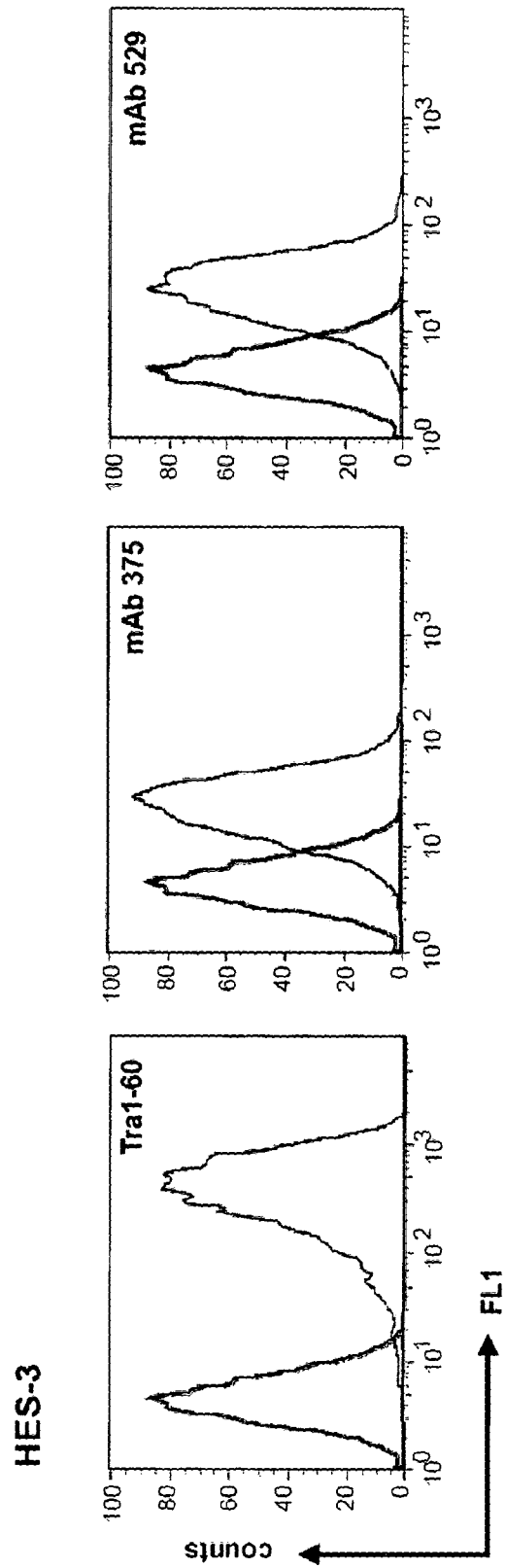
FIG. 1. shows that PHB is a surface marker for undifferentiated hESC. (A,B) Flow cytometry analysis of mAb 375 and mAb 529 for HES-3 (A) and embryoid bodies (EB) (B). The shaded and open histograms represent staining with negative control and antibodies respectively. (C) Immunoprecipitation of antigens using mAb 375 and mAb 529 and confirming their identities as prohibitin (PHB) using commercial polyclonal anti-PHB (pAb-PHB) antibody.

SEQ ID NO: 1
CKGGRAKDC

SEQ ID NO: 2
KLAKLAKKLAKLAK

SEQ ID NO: 3
CKGGRAKDC GG KLAKLAK KLAKLAK
SEQ ID NO: 3 is also referred to herein as
CKGGRAKDC-GG-(KLAKLAK)$_2$ or CKGGRAKDC-GG-$_D$(KLAKLAK)$_2$.

DETAILED DESCRIPTION OF THE INVENTION

The details of one or more embodiments of the invention are set forth in the accompanying description below including specific details of the best mode contemplated by the inventors for carrying out the invention, by way of example. It will be apparent to one skilled in the art that the present invention may be practiced without limitation to these specific details.

Preferably, a peptide as described herein is small enough to penetrate into cell-clumps or tissues, for example into samples, tissues or clumps of cells containing differentiated, partially differentiated and/or undifferentiated pluripotent stem cells. Preferably, a peptide described herein penetrates into cell-clumps or tissues better than other undifferentiated pluripotent stem cell binding moieties such as whole antibodies (e.g. mAb 375 and mAb 529) and antibody fragments.

For example a peptide may be of 10 kDa or less. A peptide may be of 10 kDa or less, 9 kDa or less, 8 kDa or less, 7 kDa or less, 6 kDa or less, 5 kDa or less, 4 kDa or less, 3 kDa or less, or about 2.5 kDa or less. In some embodiments, a peptide may be of about 2.5 kDa. Preferably, a peptide is of at least 2 kDa. The size of a peptide may be expressed as an apparent molecular weight.

A peptide described herein may have 100 amino acids or less, 90 amino acids or less, 80 amino acids or less, 70 amino acids or less, 60 amino acids or less, 50 amino acids or less, 40 amino acids or less, 30 amino acids or less, or about 25 amino acids or less. For example, a peptide described herein may have about 20 to about 30 amino acids. Preferably a peptide has at least 15 amino acids.

In some embodiments, a peptide includes a variant of one or more of SEQ ID NOs: 1 to 3. For example, a peptide may include a variant which is an amino acid sequence having at least about 70% sequence identity, at least about 75% sequence identity, at least about 80% sequence identity, at least about 85% sequence identity, or at least about 90% sequence identity or at least about 95% sequence identity with SEQ ID NO:1, SEQ ID NO:2, and/or SEQ ID NO:3. Sequence identity may be calculated along the entire length of the given sequence, i.e. with the entire length of any of SEQ ID NOs: 1 to 3.

A peptide may have a PHB-binding portion having sequence identity with the amino acid sequence as set out in SEQ ID NO: 1. For example, a peptide may have an amino acid sequence having a sequence identity of at least about 70%, at least about 75%, at least about 80%, at least about 85%, at least about 90%, at least about 95%, or about 100% with SEQ ID NO: 1.

A peptide may have a pro-apoptotic portion having sequence identity with the amino acid sequence as set out in SEQ ID NO: 2. For example, a peptide may have an amino acid sequence having a sequence identity of at least about 70%, at least about 75%, at least about 80%, at least about 85%, at least about 90%, at least about 95%, or about 100% with SEQ ID NO: 2.

In some embodiments, a pro-apoptotic PHB-binding peptide has a PHB-binding portion connected to (e.g. fused to) a pro-apoptotic portion. A PHB-binding portion and a pro-apoptotic portion may be connected via a short peptide linker, for example a GG linker. For example, a pro-apoptotic PHB-binding peptide may share sequence identity with the amino acid sequence as set out in SEQ ID NO: 3. For example, a peptide may have an amino acid sequence having a sequence identity of at least about 70%, at least about 75%, at least about 80%, at least about 85%, at least about 90%, at least about 95%, or about 100% with SEQ ID NO: 3.

Peptides may be applied to cells in effective amounts. In some embodiments, the peptide may be applied at a concentration of at least about 80 µM or one of at least about 90 µM, at least about 100 µM, at least about 110 µM, at least about 120 µM, at least about 130 µM, at least about 140 µM, at least about 150 µM, at least about 160 µM, at least about 170 µM, at least about 180 µM, at least about 190 µM, or at least about 200 µM. Peptides may be allowed to contact cells for an effective amount of time, which may be chosen from one of about 10 hours or more, 20 hours or more, 30 hours or more, 40 hours or more, 50 hours or more, 60 hours or more, 70 hours or more, 80 hours or more, 90 hours or more, 100 hours or more, 110 hours or more, 120 hours or more, 130 hours or more, 140 hours or more, 150 hours or more, 160 hours or more, 170 hours or more, 180 hours or more, 190 hours or more, or 200 hours or more.

Peptides and/or pro-apoptotic peptides or peptide components (e.g. all or part of any one of SEQ ID NO:s 1, 2 or 3) may be optical isomers, e.g. D- or L- isomers, which may be isolated. In some embodiments the peptide or peptide component may be a racemic mixture of optical isomers. In other embodiments the peptide may be the D-isomer substantially free of L-isomer (e.g. greater than 90% D-isomer). In other embodiments the peptide may be the L-isomer substantially free of D-isomer (e.g. greater than 90% L-isomer).

Percentage (%) sequence identity is defined as the percentage of amino acid residues in a candidate sequence that are identical with residues in the given listed sequence (referred to by the SEQ ID NO) after aligning the sequences and introducing gaps if necessary, to achieve the maximum sequence identity, and not considering any conservative substitutions as part of the sequence identity. Sequence identity may be calculated over the entire length, of the respective sequences.

Alignment for purposes of determining percent amino acid sequence identity can be achieved in various ways known to a person of skill in the art, for instance, using publicly available computer software such as ClustalW 1.82. T-coffee or Megalign (DNASTAR) software. When using such software, the default parameters, e.g. for gap penalty and extension penalty, are preferably used. The default parameters of ClustalW 1.82 are: Protein Gap Open Penalty=10.0, Protein Gap Extension Penalty=0.2, Protein matrix=Gonnet, Protein/DNA ENDGAP=−1, Protein/DNA GAPDIST=4.

The present disclosure describes methods of binding, identifying, isolating, separating and destroying undifferentiated pluripotent stem cells.

A pluripotent stem cell may be a mammalian pluripotent stem cell, such as a human, mouse, or rat pluripotent stem cell. In some preferred embodiments, a pluripotent stem cell is a human pluripotent stem cell. Pluripotent stem cells include embryonic stem cells and induced pluripotent stem cells. Optionally the stem cells may be non-human.

"Pluripotent stem cells" are true stem cells, with the potential to make any differentiated cell in the body. However, they cannot contribute to making the extraembryonic membranes which are derived from the trophoblast. Several types of pluripotent stem cells have been found.

The pluripotency of stem cells may be determined by use of suitable assays. Such assays may comprise detecting one or more markers of pluripotency, e.g. SSEA-1 antigen, alkaline phosphatase activity, detection of Oct-4 gene and/or protein expression, by observing the extent of teratoma formation in SCID mice or formation of embryoid bodies.

Stage-specific embryonic antigens (SSEA) are characteristic of certain embryonic cell types. Antibodies for SSEA markers are available from the Developmental Studies Hybridoma Bank (Bethesda Md.). Other useful markers are detectable using antibodies designated Tra-1-60 and Tra-1-81 (Andrews et al., Cell Linesfrom Human Germ Cell Tumors, in E. J. Robertson, 1987, supra). Human embryonic stem cells are typically SSEA-1 negative and SSEA-4 positive. hEG cells are typically SSEA-1 positive. Differentiation of pPS cells in vitro results in the loss of SSEA-4, Tra-1-60, and Tra-1-81 expression and increased expression of SSEA-1. pPS cells can also be characterized by the presence of alkaline phosphatase activity, which can be detected by fixing the cells with 4% paraformaldehyde, and then developing with Vector Red as a substrate, as described by the manufacturer (Vector Laboratories, Burlingame Calif.).

Embryonic stem cells are also typically telomerase positive and OCT-4 positive. Telomerase activity can be determined using TRAP activity assay (Kim et al., Science 266:2011, 1997), using a commercially available kit (TRAPeze® XK Telomerase Detection Kit, Cat. s7707; Intergen Co., Purchase N.Y.; or TeloTAGGG™ Telomerase PCR ELISA plus, Cat. 2,013,89; Roche Diagnostics, Indianapolis). hTERT expression can also be evaluated at the mRNA level by RT-PCR. The LightCycler TeloTAGGG™ hTERT quantification kit (Cat. 3,012,344; Roche Diagnostics) is available commercially for research purposes.

Induced pluripotent stem cells have the advantage that they can be obtained by a method that does not cause the destruction of an embryo, more particularly by a method that does not cause the destruction of a human or mammalian embryo. As such, aspects of the invention may be performed or put into practice by using cells that have not been prepared exclusively by a method which necessarily involves the destruction of human or animal embryos from which those cells may be derived. This optional limitation is specifically intended to take account of Decision G0002/06 of Nov. 25, 2008 of the Enlarged Board of Appeal of the European Patent Office.

Induced pluripotent stem cells, commonly abbreviated as iPS cells or iPSCs, are a type of pluripotent stem cell artificially derived from a non-pluripotent cell, typically an adult somatic cell, for example fibroblasts, lung or B cells, by inserting certain genes. iPS cells are reviewed and discussed in Takahashi, K. & Yamanaka (2006), Yamanaka S, et. al. (2007), Wernig M, et. al. (2007), Maherali N, et. al. (2007) and Thomson J A, Yu J, et al. (2007) and Takahashi et al., (2007).

iPS cells are typically derived by transfection of certain stem cell-associated genes into non-pluripotent cells, such as adult fibroblasts. Transfection is typically achieved through viral vectors, such as retroviruses. Transfected genes include the master transcriptional regulators Oct-3/4 (Pouf51) and Sox2, although it is suggested that other genes enhance the efficiency of induction. After 3-4 weeks, small numbers of transfected cells begin to become morphologically and biochemically similar to pluripotent stem cells, and are typically isolated through morphological selection, doubling time, or through a reporter gene and antibiotic infection.

Some aspects and embodiments of the present invention are concerned with the use of pluripotent cells. Embryonic stem cells and induced pluripotent stem cells are described as examples of such cells.

Embryonic stem cells have traditionally been derived from the inner cell mass (ICM) of blastocyst stage embryos (Evans, M. J., and Kaufman, M. H. (1981). Establishment in culture of pluripotential cells from mouse embryos. Nature 292, 154-156. Martin, G. R. (1981). Isolation of a pluripotent cell line from early mouse embryos cultured in medium conditioned by teratocarcinoma stem cells. Proc. Natl. Acad. Sci. USA 78, 7634-7638. Thomson, J. A., Itskovitz-Eldor, J., Shapiro, S. S., Waknitz, M. A., Swiergiel, J. J., Marshall, V. S., and Jones, J. M. (1998). Embryonic stem cell lines derived from human blastocysts. Science 282, 1145-1147). In isolating embryonic stem cells these methods may cause the destruction of the embryo.

Several methods have now been provided for the isolation of pluripotent stem cells that do not lead to the destruction of an embryo, e.g. by transforming adult somatic cells or germ cells. These methods include:

1. Reprogramming by nuclear transfer. This technique involves the transfer of a nucleus from a somatic cell into an oocyte or zygote. In some situations this may lead to the creation of an animal-human hybrid cell. For example, cells may be created by the fusion of a human somatic cell with an animal oocyte or zygote or fusion of a human oocyte or zygote with an animal somatic cell.

2. Reprogramming by fusion with embryonic stem cells. This technique involves the fusion of a somatic cell with an embryonic stem cell. This technique may also lead to the creation of animal-human hybrid cells, as in 1 above.

3. Spontaneous re-programming by culture. This technique involves the generation of pluripotent cells from non-pluripotent cells after long term culture. For example, pluripotent embryonic germ (EG) cells have been generated by long-term culture of primordial germ cells (PGC) (Matsui et al., Derivation of pluripotential embryonic stem cells from murine primordial germ cells in culture. Cell 70, 841-847, 1992, incorporated herein by reference). The development of pluripotent stem cells after prolonged culture of bone marrow-derived cells has also been reported (Jiang et al., Pluripotency of mesenchymal stem cells derived from adult marrow. Nature 418, 41-49, 2002, incorporated herein by reference). They designated these cells multipotent adult progenitor cells (MAPCs). Shinohara et al also demonstrated that pluripotent stem cells can be generated during the course of culture of germline stem (GS) cells from neonate mouse testes, which they designated multipotent germline stem (mGS) cells (Kanatsu-Shinohara et al., Generation of pluripotent stem cells from neonatal mouse testis. Cell 119, 1001-1012, 2004).

4. Reprogramming by defined factors. For example the generation of iPS cells by the retrovirus-mediated introduction of transcription factors (such as Oct-3/4, Sox2, c-Myc, and KLF4) into mouse embryonic or adult fibroblasts, e.g. as described above. Kaji et al (Virus-free induction of pluripotency and subsequent excision of reprogramming factors. Nature. Online publication Mar. 1, 2009) also describe the non-viral transfection of a single multiprotein expression vector, which comprises the coding sequences of c-Myc, Klf4, Oct4 and Sox2 linked with 2A peptides, that can reprogram both mouse and human fibroblasts. iPS cells produced with this non-viral vector show robust expression of pluripotency markers, indicating a reprogrammed state confirmed functionally by in vitro differentiation assays and formation of adult chimaeric mice. They succeeded in establishing reprogrammed human cell lines from embryonic fibroblasts with robust expression of pluripotency markers.

Methods 1-4 are described and discussed by Shinya Yamanaka in Strategies and New Developments in the Generation of Patient-Specific Pluripotent Stem Cells (Cell Stem Cell 1, July 2007 [a]2007 Elsevier Inc), incorporated herein by reference.

5. Derivation of hESC lines from single blastomeres or biopsied blastomeres. See Klimanskaya I, Chung Y, Becker S, Lu S J, Lanza R. Human embryonic stem cell lines derived from single blastomeres. Nature 2006; 444:512, Lei et al Xeno-free derivation and culture of human embryonic stem cells: current status, problems and challenges. Cell Research (2007) 17:682-688, Chung Y, Klimanskaya I, Becker S, et al. Embryonic and extraembryonic stem cell lines derived from single mouse blastomeres. Nature. 2006; 439:216-219. Klimanskaya I, Chung Y, Becker S, et al. Human embryonic stem cell lines derived from single blastomeres. Nature. 2006; 444:481-485. Chung Y, Klimanskaya I, Becker S, et al. Human embryonic stem cell lines generated without embryo destruction. Cell Stem Cell. 2008; 2:113-117 and Dusko llic et al (Derivation of human embryonic stem cell lines from biopsied blastomeres on human feeders with a minimal exposure to xenomaterials. Stem Cells And Development—paper in pre-publication), all incorporated herein by reference.

6. hESC lines obtained from arrested embryos which stopped cleavage and failed to develop to morula and blastocysts in vitro. See Zhang X, Stojkovic P, Przyborski S, et al. Derivation of human embryonic stem cells from developing and arrested embryos. Stem Cells 2006; 24:2669-2676 and Lei et al Xeno-free derivation and culture of human embryonic stem cells: current status, problems and challenges. Cell Research (2007) 17:682-688, both incorporated herein by reference.

7. Parthogenesis (or Parthenogenesis). This technique involves chemical or electrical stimulation of an unfertilised egg so as to cause it to develop into a blastomere from which embryonic stem cells may be derived. For example, see Lin et al. Multilineage potential of homozygous stem cells derived from metaphase II oocytes. Stem Cells. 2003; 21(2):152-61 who employed the chemical activation of nonfertilized metaphase II oocytes to produce stem cells.

8. Stem cells of fetal origin. These cells lie between embryonic and adult stem cells in terms of potentiality and may be used to derive pluripotent or multipotent cells. Human umbilical-cord-derived fetal mesenchymal stem cells (UC fMSCs) expressing markers of pluripotency (including Nanog, Oct-4, Sox-2, Rex-1, SSEA-3, SSEA-4, Tra-1-60, and Tra-1-81, minimal evidence of senescence as shown by (3-galactosidase staining, and the consistent expression of telomerase activity) have been successfully derived by Chris H. Jo et al (Fetal mesenchymal stem cells derived from human umbilical cord sustain primitive characteristics during extensive expansion. Cell Tissue Res (2008) 334:423-433, incorporated herein by reference). Winston Costa Pereira et al (Reproducible methodology for the isolation of mesenchymal stem cells from human umbilical cord and its potential for cardiomyocyte generation J Tissue Eng Regen Med 2008; 2: 394-399, incorporated herein by reference) isolated a pure population of mesenchymal stem cells from Wharton's jelly of the human umbilical cord. Mesenchymal stem cells derived from Wharton's jelly are also reviewed in Troyer & Weiss (Concise Review: Wharton's Jelly-Derived Cells Are a primitive Stromal Cell Population. Stem Cells 2008:26:591-599). Kim et al (Ex vivo characteristics of human amniotic membrane-derived stem cells. Cloning Stem Cells 2007 Winter; 9(4):581-94, incorporated herein by reference) succeeded in isolating human amniotic membrane-derived mesenchymal cells from human amniotic membranes. Umbilical cord is a tissue that is normally discarded and stem cells derived from this tissue have tended not to attract moral or ethical objection.

The present invention includes the use of pluripotent stem cells obtained from any of these sources or created by any of these methods. In some embodiments, the pluripotent cells used in the methods of the present invention have been obtained by a method that does not cause the destruction of an embryo. More preferably in some embodiments, the pluripotent cells used in the methods of the present invention have been obtained by a method that does not cause the destruction of a human or mammalian embryo. As such, methods of the invention may be performed using cells that have not been prepared exclusively by a method which necessarily involves the destruction of human embryos from which those cells may be derived. This optional limitation is specifically intended to take account of Decision G0002/06 of Nov. 25, 2008 of the Enlarged Board of Appeal of the European Patent Office.

The method may be performed in vitro. For example, a sample may be from a mammalian embryo, may be mammalian embryonic tissue, or may be a sample of cells cultivated in vitro. A sample may contain undifferentiated pluripotent stem cells, pluripotent stem cells which are differentiated, pluripotent stem cells which are undergoing differentiation and/or non-pluripotent cells. A sample may contain cells or may be likely to contain cells which have the potential to form teratomas, for example, human pluripotent stem cells. A sample may contain human pluripotent stem cells and/or cells differentiated from human pluripotent stem cells. For example, a sample may comprise hESCs and/or IPSCs. Furthermore, a sample may contain cells differentiated from hESCs and/or IPSCs.

Materials and Methods

Cell Culture

Human embryonic stem cell line, HES-3, was obtained from ES Cell International (ESI, Singapore, http://escellinternational.com). The cells were cultured at 37° C., 5% $CO_2$, on matrigel-coated culture dishes supplemented with conditioned media from immortalized mouse embryonic fibroblast, ΔE-MEF. The media used for culturing hESC was Knockout (KO) media containing 85% KO-DMEM (DMEM, Dulbecco's modified Eagle's medium) supplemented with 15% KO serum replacer, 1 mM L-glutamine, 1% non-essential amino acids, 0.1 mM 2-mercaptoethanol, and 10 ng/ml basic fibroblast growth factor (FGF-2; Invitrogen, Carlsbad, Calif., http://www.invitrogen.com). The cells were treated with collagenase IV (200 U/ml) or TrypLE Express solution (Invitrogen) and dissociated into small clumps or single cells respectively by repeated pipetting. The cells were then reseeded onto matrigel-coated plates at a passage ratio 1:4.

For FGF-2 deprived cultures, HES-3 was cultured as described above in the absence of FGF-2 for either 7 or 14 days followed by re-stimulation with 10 ng/ml of FGF-2 for indicated periods of time. Cells were subsequently harvested for flow cytometry or western blot analysis.

Induced pluripotent stem cell line, ESIMR90, derived from lung fibroblasts, was obtained from James Thomson (18). ESIMR90 was cultured as per hESC cultures, with the exception of supplementing cultures with 100 ng/ml of FGF-2. For FGF-2 starved cultures, cells were maintained without FGF-2 as mentioned above.

To induce hESC differentiation in vitro, HES-3 cells were harvested as clumps and cultured as embryoid bodies (EB) for 8 days in EB-medium (80% KO-DMEM, 20% fetal bovine serum, 25 U/ml penicillin, 25 g/ml streptomycin, 2 mM L-glutamine, 0.1 mM non-essential amino acids, and 0.1 mM 2-mercaptoethanol) on non adherent suspension culture dishes (Corning Life Sciences, Acton, Mass., http://www.corning.com/lifesciences). Subsequently, the EB were dissociated with trypsin and plated on gelatinized culture dishes in EB-medium for an additional 7 days.

Human fetal lung fibroblast cell line, IMR-90 (CCL-186), was purchased from American Type Culture Collection and cultured according to the supplier's instructions.

Flow Cytometry Analysis

Cells were harvested as single cell suspensions using trypsin, resuspended at $2 \times 10^5$ cells per 10 μl volume in 1% bovine serum albumin (BSA)/PBS and incubated for 45 min with each mAb clone (100 ul culture supernatant) or monoclonal TRA-1-60 antibody. (12.5 ug/ml; Chemicon, Temecula, Calif. http://www.chemicon.com). Cells were then washed with cold 1% BSA/PBS, and further incubated for 15 min with 1:500 dilution of fluorescein isothiocyanate (FITC)-conjugated goat α-mouse antibody (DAKO, Glostrup, Denmark, http://www.dako.com). After incubation, the cells were again washed and resuspended in 1% BSA/PBS for analysis on a FACScan (Becton, Dickinson and Company, Franklin Lakes, N.J., http://www.bd.com).

Immunocytochemistry

HES-3 grown on matrigel coated poly-1-lysine glass coverslips were fixed with 4% paraformaldehyde for 1 h, blocked using 3% BSA/PBS for 1 h, followed by incubating with polyclonal antibody (pAb) to human prohibitin (PHB, R&D Systems Inc., Minneapolis, http://www.rndsystems.com, AF3470) and monoclonal Oct-4 antibody (Santa Cruz, USA, http:///www.scbt.com) at 1:50 dilution at room temperature for 1 h. Localization of antibodies was detected using either AlexaFluor594 conjugated anti-mouse or AlexaFluor488 conjugated anti-goat antibodies (1:500; Invitrogen, Carlsbad, Calif., http://www.invitrogen.com) and visualized using Carl Zeiss LSM510 META confocal imaging system (Zeiss, Germany, http://www.zeiss.de).

Immunoprecipitation hESC were grown to confluence in 6 cm culture dishes (BD Biosciences, USA, http://www.bdbiosciences.com) and the membrane fraction was isolated using ProteoPrep Membrane Extraction kit (Sigma Aldrich, USA http://www.siamaaldrich.com), following the manufacturer's instructions. The membrane fraction was used directly for immunoprecipitation (IP). IP of the antigen was carried out using the automated Phynexus MEA system (Phynexus, Inc., San Jose, Calif., http://www.phynexus.com). Briefly, biotinylated anti-mouse IgM antibody (1:10; Open Biosystems, USA, http://www.openbiosystems.com) was captured onto Streptavidin PhyTip column before binding to mAb 375 or mAb 529. After washing away unbound proteins with 2% Triton/PBS, the membrane fraction was passed through the column. The bound proteins were then eluted using elution buffer (200 mM $NaH_2PO_4$/140 mM NaCl pH 2.5) and neutralized immediately with 1 M Tris-Cl pH 9.0.

Western Blot Analysis

Eluates from IP were resolved on a 4-12% Bis-Tris gradient gel (Invitrogen, Carlsbad, Calif., http://www.invitrogen.com) under reducing conditions followed by either western blotting or silver staining. For western blotting, resolved proteins were transferred onto PVDF membrane (Millipore, Billerica, Mass., http://www.millipore.com) at 110 V for 1 h and immunoblotted with either mAb 375 culture supernatant, mAb 529 culture supernatant or goat pAb to human PHB (200 ng/ml, R&D Systems Inc., Minneapolis, http://www.rndsystems.com, AF3470) followed by horseradish peroxidase (HRP)-conjugated goat anti-mouse or rabbit anti-goat antibodies at 1:10,000 dilution. (DAKO, Glostrup, Denmark, http://www.dako.com). Binding of HRP-conjugated secondary antibodies were visualized by ECL detection using Immobilon Western HRP Substrate (Millipore, Billerica, Mass., http://www.millipore.com). Silver staining was performed using SilverQuest silver staining kit (Invitrogen, Carlsbad, Calif., http://www.invitrogen.com) according to the manufacturer's protocol and the protein band which corresponds to the antigen band on western blot was excised for mass spectrometry analysis.

hESC cultured under various conditions were lysed and clarified via centrifugation before quantifying with the DC protein assay (Biorad, http://www.bio-rad.com). 20 ug of total protein from each condition was resolved and transferred onto membrane as described above. The resolved proteins were then immunoblotted with anti-actin (1:10,000; Abcam, http://www.abcam.com), anti-total ERK (1:1000; Sigma Aldrich) and anti-phospho-ERK (1:5000; Sigma Aldrich) antibodies. The protein bands were visualized using either ECL Plus detection reagent (Amersham, GE Healthcare, UK, http://www.gehealthcare.com) or LI-COR ODYSSY imaging system (LI-COR Biosciences, Nebraska, http://www.licor.com).

SU5402 Inhibitor Studies

Efficacy of SU5402 (Calbiochem, San Diego, USA, http://www.emdbiosciences.com) was determined by culturing hESC in absence of FGF-2 for 5 days, followed by incubating with 20 μM or 30 μM of SU5402 for 2 h before inducing the treated cultures with FGF-2 for 15 min. Cells were then lysed and the lysates were analyzed using western blot analysis.

To observe the effect of SU5402 on expression of PHB in hESC, cells were seeded and allowed to adhere for 24 h before culturing them in the presence of SU5402 at concentrations of 20 μM or 30 μM for 7 days. Control cells were cultured similarly in the presence of the vehicle control, DMSO instead. Cells were subsequently harvested for flow cytometry analysis.

Growth Curve

HES-3 and IMR-90 cells were cultured in 24 wells culture dishes supplemented with either 100 μM PHB-targeting pro-apoptotic peptide (CKGGRAKDC-GG-$_D$(KLAKLAK)$_2$ (SEQ ID NO:3)>90% purity; Sigma Aldrich) or 0.2% DMSO as control. Cultures were induced every 48 h and harvested daily for cell count. Cell numbers were determined using NucleoCounter according to the manufacturer's recommendations (Chemometec, Denmark, http://http://www.chemometec.com). The growth curves were generated by plotting viable cell number vs time. Specific growth rate, μ, was calculated as the gradient of the exponential phase, determined by plotting ln(cell number) vs time. Triplicates were done for each set of data.

Viability was determined using Propidium Iodide (PI) assay, where cells were trypsinized and resuspended in binding buffer (10 mM HEPES/NaOH, 140 mM NaCl and 2.5 mM $CaCl_2$) containing 1.25 mg/ml of PI. The cells were incubated at room temperature for 15 min before analyzing on the flow cytometer.

Detection of Caspase-3 Activity

To detect caspase-3 activity in treated hESC, cells grown in 24 wells were incubated with 5 μM of NucView 488 Caspase-3 substrate (Biotium Inc, www.biotium.com) and sulforhodamine 101-annexin V (1.25 ug/ml; Biotium Inc) at room temperature for 30 min. Cells were then washed once with PBS and examined under the Olympus IX70 fluorescence microscope (Olympus, http://www.olvmousamerica.com). For flow cytometry analysis, hESC was trypinsized before resuspending cells in PBS containing caspase-3 substrate and annexin V reagents.

TUNEL assay

Nuclear DNA fragmentation was measured via a TUNEL (Terminal deoxynucleotidyl transferase dUTP nick end labeling) assay kit (Promega, Madison, Wis., http://www.promega.com). Cells were harvested from each condition and fixed in 1% paraformaldehyde for 20 min on ice before permeabilizing them with ice-cold 70% ethanol at 20° C. overnight. Subsequently, the cells were washed with PBS and incubated in 80 μl of equilibration buffer for 5 min at room temperature. The cells were pelleted down and resuspended in 50 μl of incubation buffer containing nucleotides and rTdT enzyme, followed by incubation at 37° C. for 1 h. The reaction was quenched using 20 mM EDTA and cells were resuspended in 0.1% Triton/0.5% BSA/PBS before analyzing on the flow cytometer. The green fluorescence of fluorescein-12-dUTP was detected in the FL1 channel.

Results

Identification of mAb 375 and mAb 529 Antigen Target on hESC

Figure 8A:
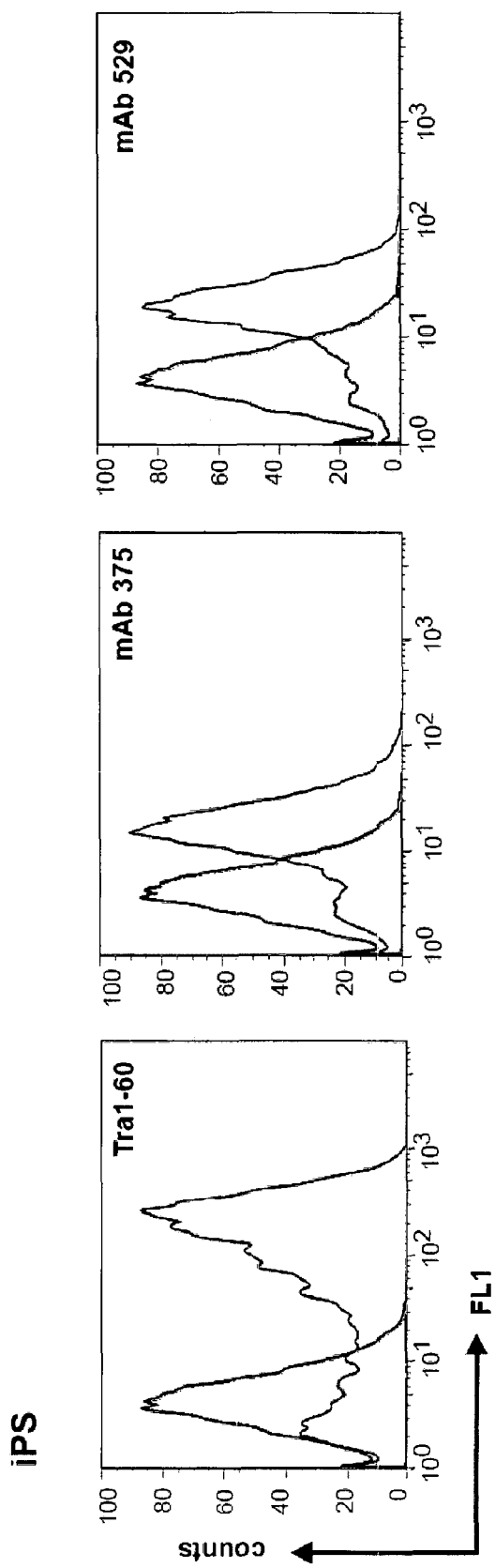
FIG. 8. shows that PHB is a surface marker for iPS cells. (A,B) Flow cytometry analysis of mAb 375 and mAb 529 for iPS (A) and iPS derived embryoid bodies (EB) (B). The shaded and open histograms represent staining with negative control and antibodies respectively.

To determine the specificity of antibodies against hESC, we examined the reactivity of mAb 375 and mAb 529 to undifferentiated HES-3 and HES-3 derived embryoid bodies (EB) using flow cytometry analysis. mAb 375 and mAb 529 exhibit strong reactivity to hESC expressing the pluripotent marker, Tra1-60 (FIG. 1A). However, reactivity was significantly reduced when hESC were induced to form EB, suggesting that mAb 375 and mAb 529 bind specifically to pluripotent hESC and the expression of the surface antigen decreases as the cells differentiate (FIG. 1B). Similar mAb reactivity was also observed on pluripotent iPS cells and iPS derived EBs respectively (FIG. 8A).

To identify their antigen targets, immunoprecipitation of HES-3 membrane fraction with both mAbs were performed and proteins eluted were resolved and probed with the respective mAbs. An antigen band of ~30 kDa was observed for both mAbs (FIG. 1C, lane 2 and 4). The corresponding bands on a silver stained gel was excised and identified out by mass spectrometry.

Figure 10:
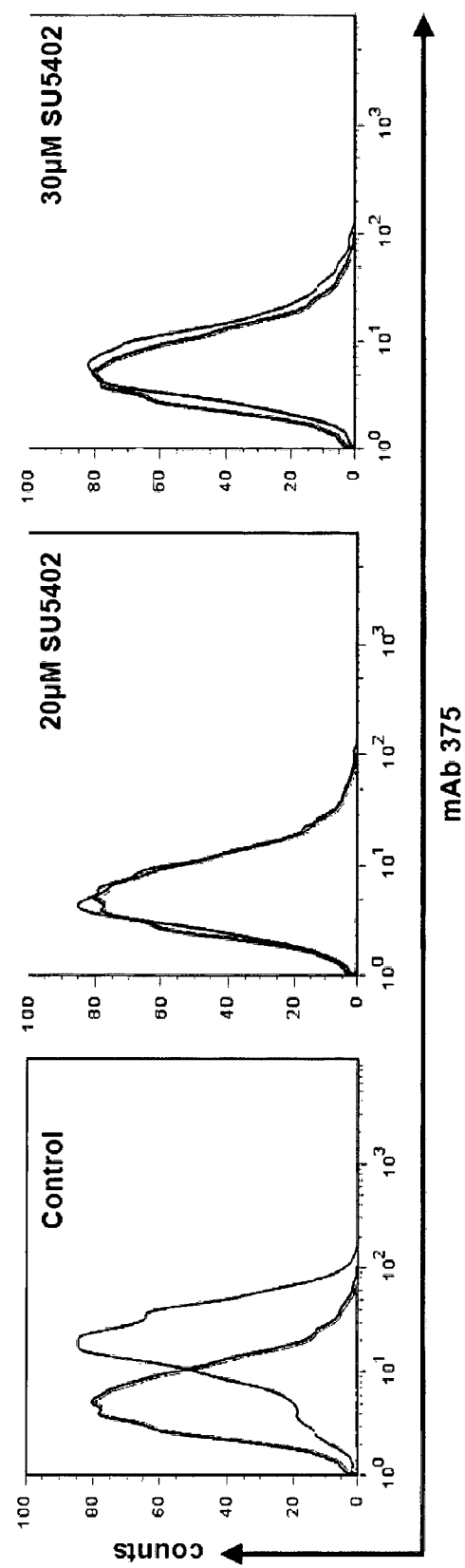
FIG. 10. shows that MAPK activity level in iPS cells affects PHB surface expression. PHB surface expression level in SU5402 treated iPS cultures were determined using flow cytometry analysis. The shaded and open histograms represent staining with negative control and mAb 375 respectively.

From protein database search with the peptides obtained, the antigen bands from both mAbs were identified as prohibitin (PHB; Accession No. NM_002634.2). In order to validate identity of the antigen target, immunoprecipitation with mAb 375 and mAb 529 were repeated and the eluate from the column was probed with commercially-available antibody to PHB (pAb-PHB) (FIG. 10, lane 3 and 5). From the Western blot, all three antibodies detected identical protein bands of comparable molecular weight in the IP eluate, thus confirming the identity of PHB.

Figure 2A:
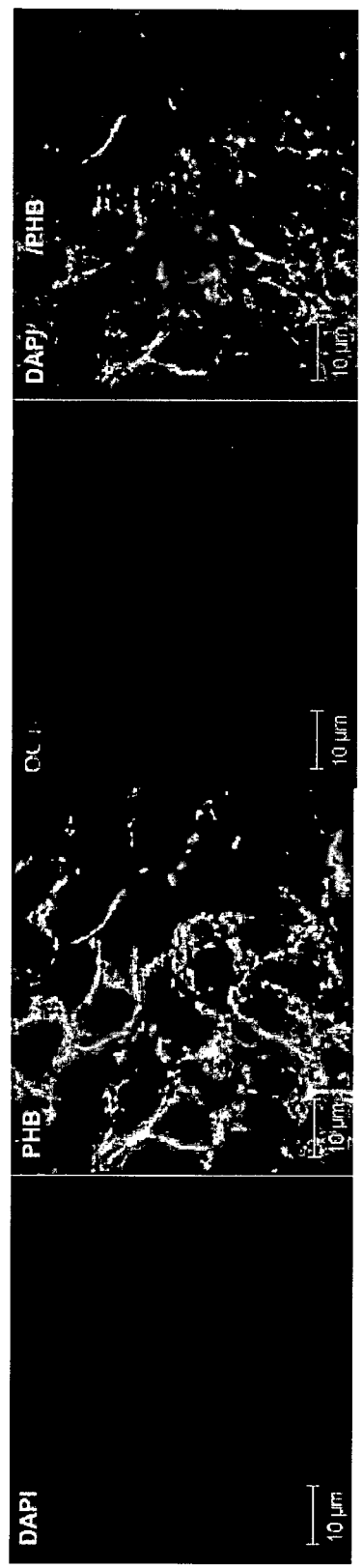
FIG. 2. shows that PHB is localized to surface membrane of Oct-4 expressing pluripotent hESC. (A,B) Representative images showing PHB immunostaining using commercial PHB antibody with the pluripotent marker OCT-4 in HES-3 (A) and plated EB (B) cultures. Scale bar corresponds to 10 µm.
Figure 2B:
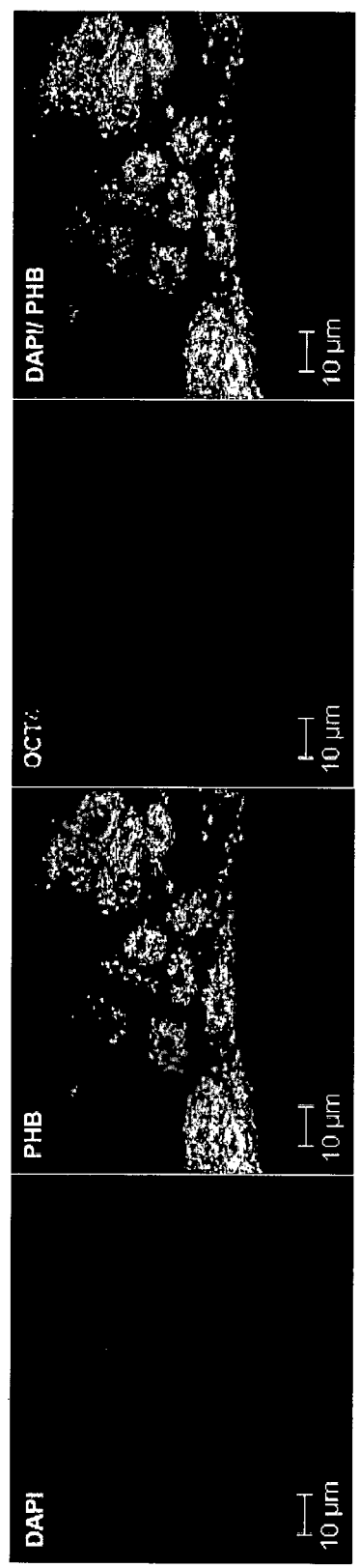
Figure 8B:
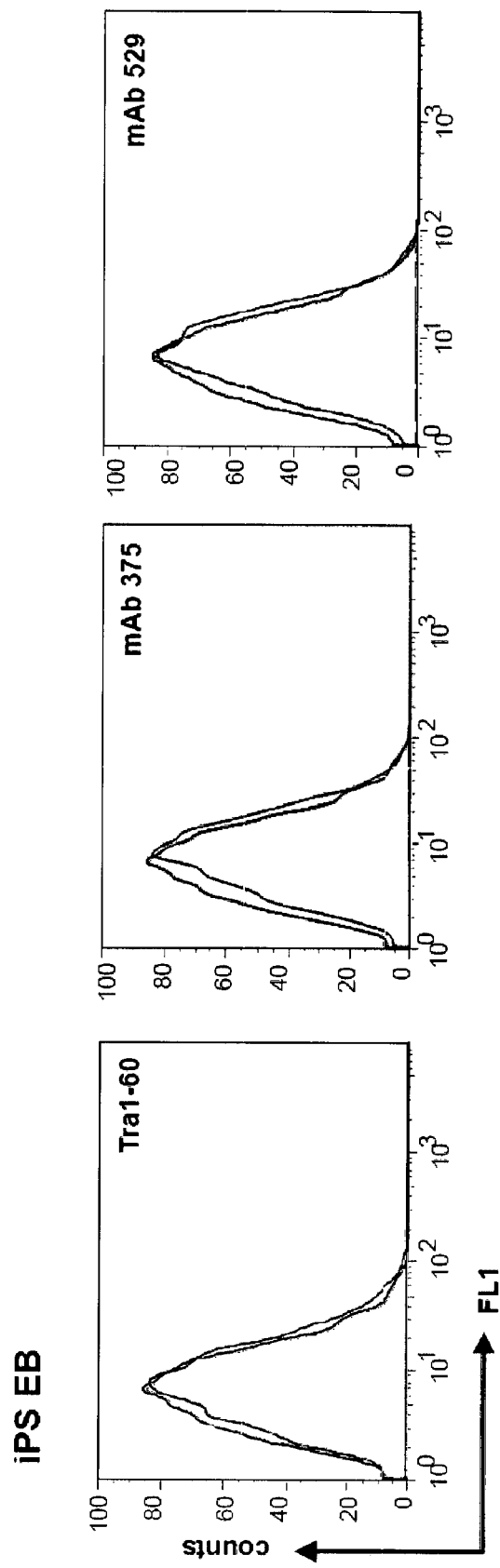
Figure 9:
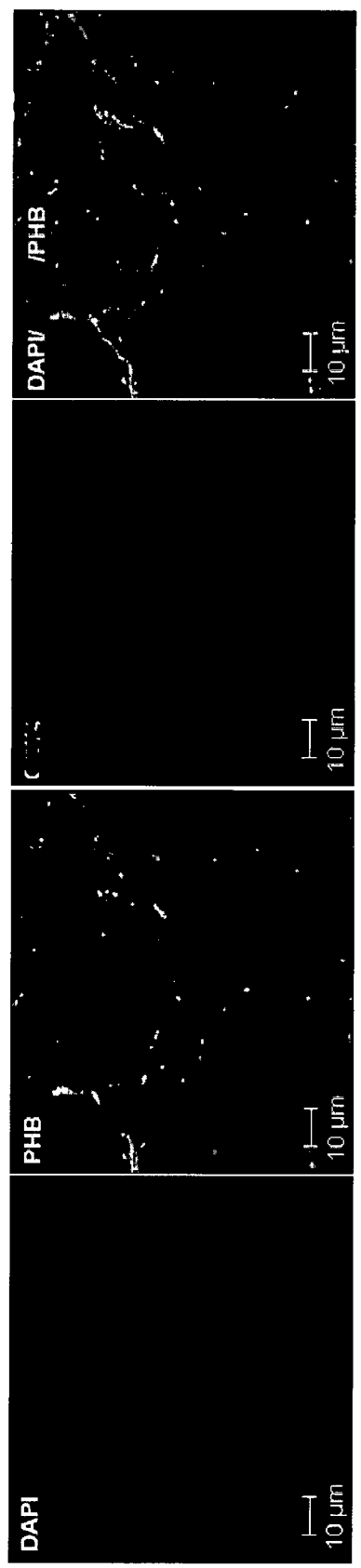
FIG. 9. shows that PHB is localized to surface of Oct-4 expressing iPS cells. Representative images showing PHB immunostaining using commercial PHB antibody with the pluripotent marker OCT-4 in iPS cultures. Scale bar corresponds to 10 µm.

After identifying the antigen targets of mAb 375 and mAb 529 as PHB, we proceeded with immunostaining of HES-3 cells with pAb-PHB to verify the presence of PHB on hESC surface. In HES-3 and ESIMR90 cells, PHB was colocalized to cells expressing pluripotent marker OCT-4 and it is located predominantly on the plasma membrane (FIG. 2A and FIG. 8B). However, PHB is localized in the nucleus when HES-3 was differentiated to form EBs (FIG. 2B).

Effect of MAPK Activation on PHB Surface Expression in hESC

Figure 3A:
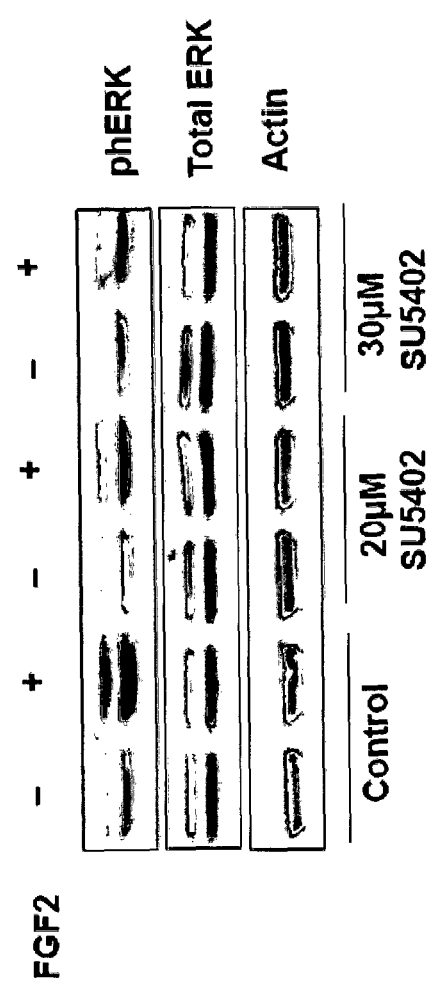
FIG. 3. shows that MAPK activity level in hESC affects PHB surface expression. (A) Effective inhibition of MAPK activity with addition of FGFR inhibitor, SU5402 (B) PHB surface expression level in SU5402 treated HES-3 cultures were determined using flow cytometry analysis. The shaded and open histograms represent staining with negative control and mAb 375 respectively.
Figure 3B:
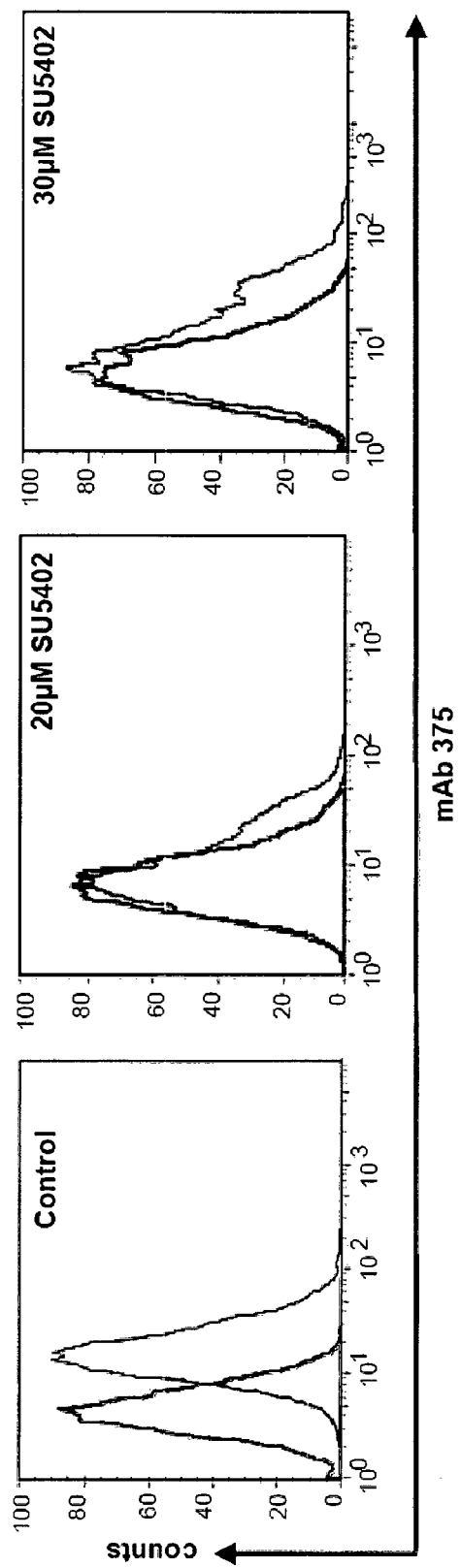

A recent report by Rajalingam et al (13) describes an involvement of PHB in EGF-induced MAPK activation in HeLa cells. In order to study the role of PHB in MAPK pathway in hESC, we blocked FGFR signaling with SU5402, which lowered MAPK activity, and examined the effects on PHB surface expression. HES-3 cultures starved of FGF-2 for 5 days were pretreated with 20 μM and 30 μM of SU5402 for 2 h before stimulating with 10 ng/ml of FGF-2 for 15 min. Results from western blot indicated suppression of ERK phosphorylation (FIG. 3A), thus confirming the inhibitory effect of SU5402 on MAPK pathway. By flow cytometry, cells treated with both concentrations of SU5402 inhibitor also had a down-regulated surface expression of PHB suggesting an effect of MAPK activity on PHB surface expression (FIG. 3B). Similar results were observed for SU5402-treated ESIMR90 cultures (FIG. 10).

Figure 4A:
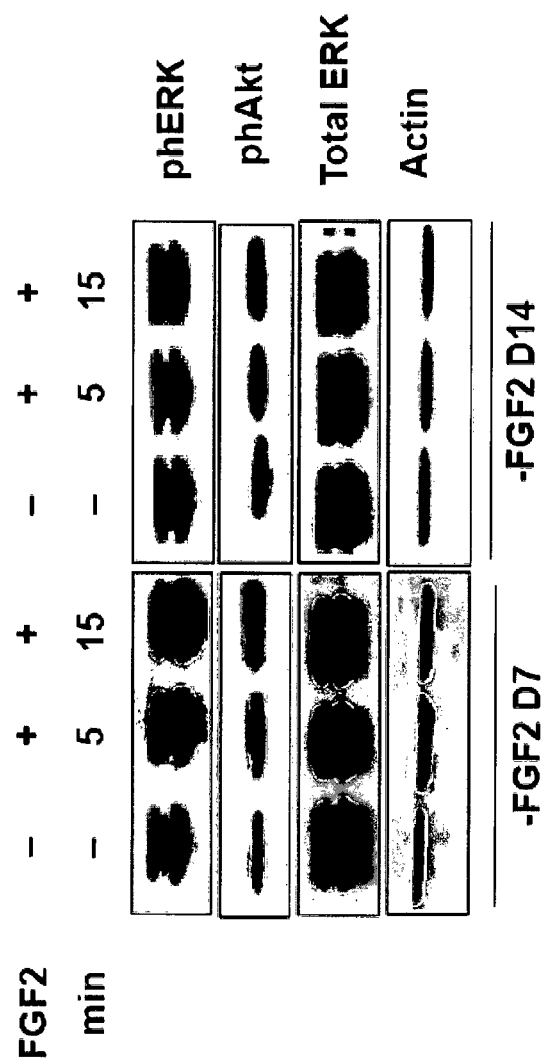
FIG. 4. shows that activation of MAPK is essential for maintaining PHB surface expression. (A) ph-ERK, ph-Akt and total ERK expression levels of re-stimulated FGF-2 deprived HES-3 cultures were determined by western blot. Actin was used as a loading control. (B) Flow cytometry analysis of surface PHB on re-stimulated FGF-2 deprived HES-3 cells. The shaded and open histograms represent staining with negative control and mAb 375 respectively.
Figure 4B:
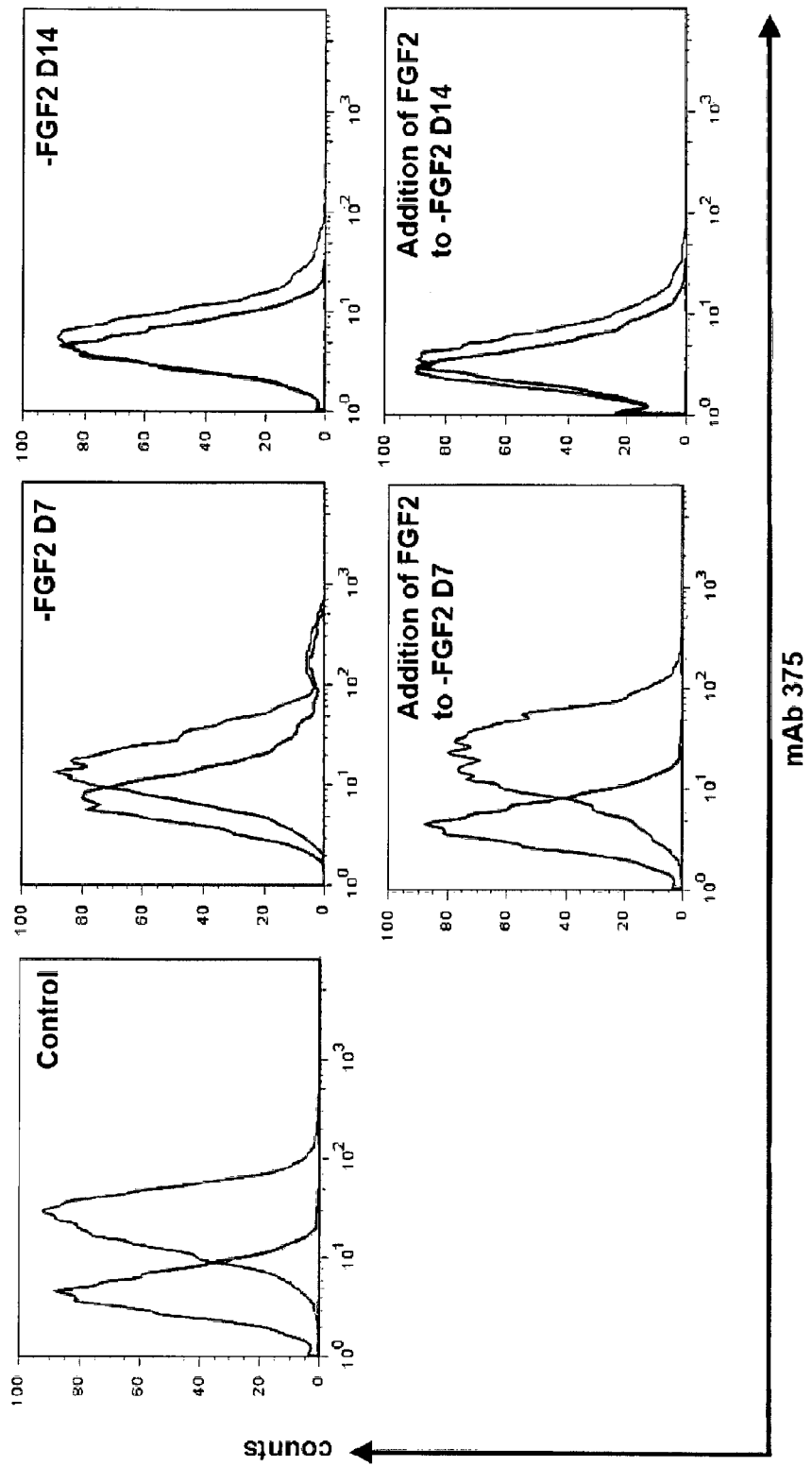

To support this finding, hESC were starved of FGF-2 for 7 days to reduce ERK phosphorylation before re-stimulating the cultures with 10 ng/ml of FGF-2 for another 7 days. An increase in ERK phosphorylation was observed after FGF-2 re-stimulation and the expression level of PHB was restored to levels comparable to control cells after 7 days. In contrast, we failed to observe a similar increase in ERK phosphorylation or PHB expression in hESC re-stimulated with FGF-2 after 14 days of FGF-2 deprivation. It is interesting to note that the Akt signaling remains responsive to FGF-2 stimulation under both conditions (FIG. 4A), thus it is unlikely to cause the discrepancy in PHB restoration. Taken together, the results suggest the activation of MAPK signaling is important in maintaining PHB surface expression in hESC.

Effect of PHB-Targeted Pro-Apoptotic Peptide on hESC

In a recent study done by Kolonin et al (11), they identified a peptide motif, CKGGRAKDC (SEQ ID NO: 1), which targets PHB present in the vasculature of white adipose tissue in mice. To induce fat resorption, they coupled a pro-apoptotic peptide, $(KLAKLAK)_2$, (SEQ ID NO: 2) to the PHB homing peptide motif, which leads to the ablation of adipose tissue and a rapid obesity reversal. This strategy could potentially be used to remove residual hESC after differentiation.

Figure 5A:
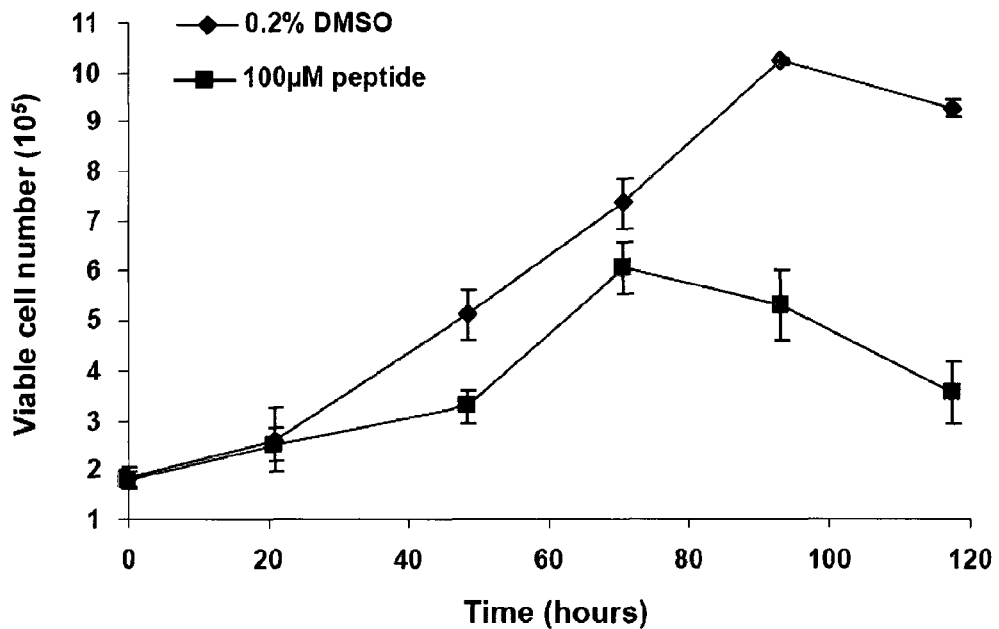
FIG. 5. shows that PHB targeting pro-apoptotic peptide induces cell death in hESC. (A,B) Growth curves of peptide and DMSO treated HES-3 cultures. (C) The graph shows the relative viability of peptide treated HES-3 cells (white bar) and control with DMSO (grey bar). Relative viability (%) was calculated as ratio of the viability of peptide-treated cells to the viability of control cells. Error bars represent standard deviation from three determinations.
Figure 5B:
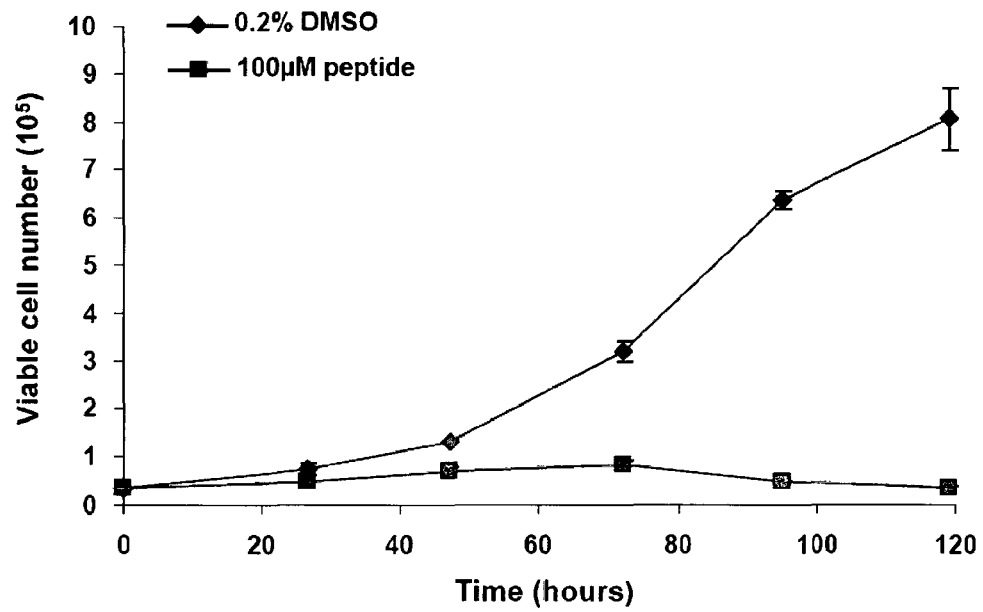
Figure 5C:
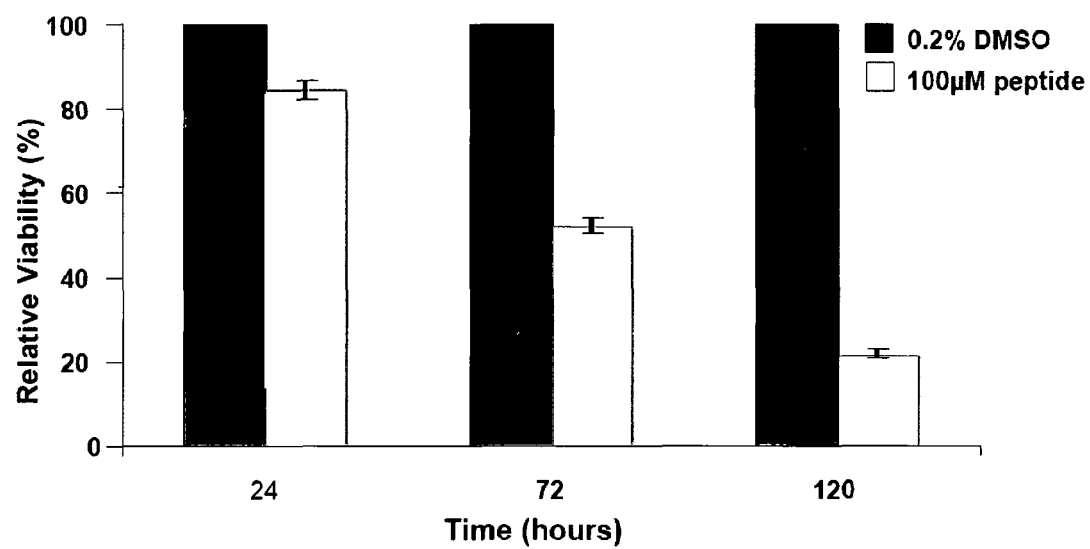
Figure 11A:
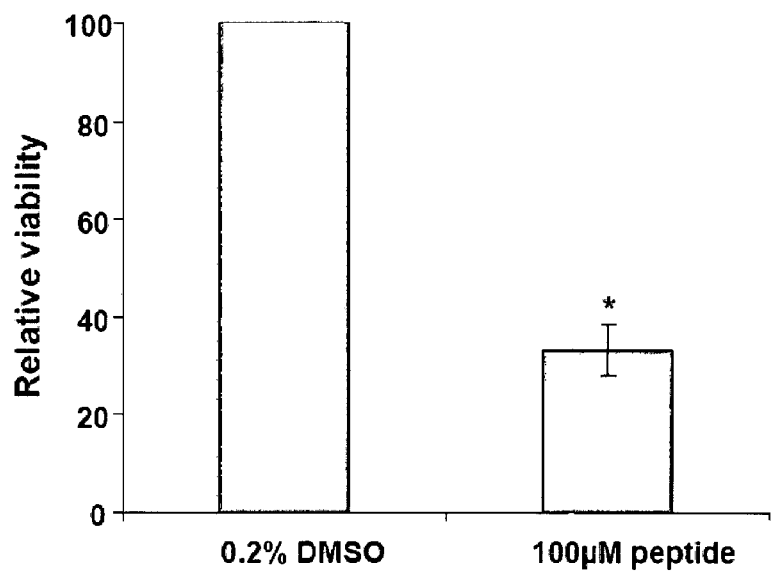
FIG. 11. shows that peptide-treated iPS cells exhibit characteristics of apoptosis. (A) The graph shows the relative viability of iPS cells treated with peptide for 72 h. (B) iPS cells pretreated with peptide (top panel) or DMSO (bottom panel) for 24 h were stained using Texas-Red Annexin V and cell-permeable fluorogenic caspase-3 substrate. Scale bar corresponds to 20 µm. (C) Population of peptide-treated iPS cells expressing elevated caspase-3 activity. Error bars represent standard deviation from three determinations. * indicates significant difference over control ($p<0.01$).

To investigate the effect of PHB-targeted apoptotic peptide in hESC, we treated clump cultures with 100 μM of peptide and examined the viable cell numbers and viability over 7 days. From FIG. 5A-C, it is apparent that supplementing hESC with 100 μM of peptide led to a decrease in growth rate and viability over time compared to the control supplemented with 0.2% DMSO. The specific growth rate for peptide-treated hESC was 0.0113 $hr^{-1}$ ($t_d$=61.3 hrs), which is significantly lower compared to control cells (0.019 $hr^{-1}$); $t_d$=36.5 hrs). Furthermore, we also observed the initiation of death phase in peptide-treated hESC culture occurred at 70 hours while the control culture was still proliferating exponentially (FIG. 5A). The effect of cell killing of hESC were more apparent when the peptide was supplemented to TrypLE passaged cultures, where we observed minimal growth compared to the control (FIG. 5B). This could be due to an increase in accessibility of the peptide to hESC when they were passaged as single cells using TrypLE solution. We also observed a decline in viability of peptide-treated hESC over time, as measured by PI uptake (FIG. 5C). The relative viability reduced from 84.7% at 24 h to 52.2% and 21.7% after 72 and 120 h treatment with the peptide. Similar effect was observed in peptide-treated ESIMR90 cultures (FIG. 11A), where relative viability reduced to 33.4% after 72 h of peptide treatment. These results clearly demonstrate the ability of the peptide to induce cell death in hESC.

Figure 6:
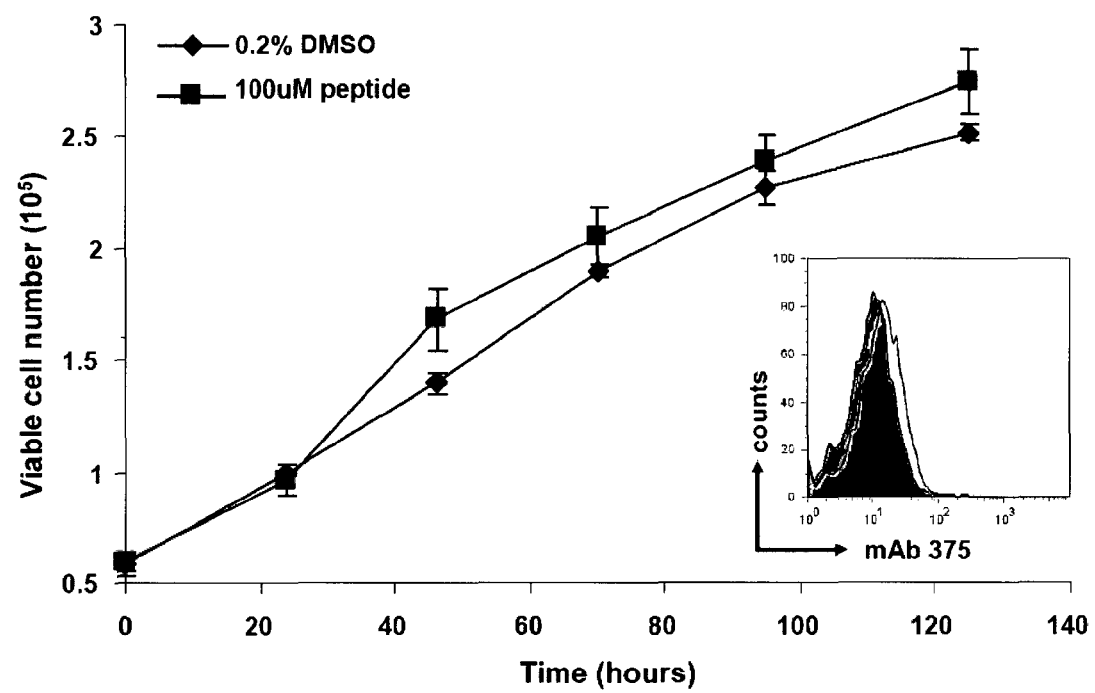
FIG. 6. shows that cell killing effect of peptide is specific to PHB expressing cells. (A) Growth curves of IMR-90 cells treated with either 100 µM of peptide or 0.2% DMSO as vehicle control. Error bars represent standard deviation from three determinations. Inset: The shaded and open histogram represents IMR-90 staining with negative control and mAb 375 respectively.

After validating the efficacy of the peptide, we treated IMR-90 cells with 100 μM of peptide to evaluate its specificity. IMR-90 cells were used as negative control because they do not express PHB on the cell surface, as shown by their weak reactivity with mAb 375 (FIG. 6). As expected, the growth rate of peptide-treated IMR-90 (μ=0.0167 $hr^{-1}$) was comparable to its control with 0.2% DMSO (μ=0.0183 $hr^{-1}$). Thus, this result is indicative that the cell killing properties of the peptide are specific and are only targeted to cells expressing PHB on their surface.

Figure 7A:
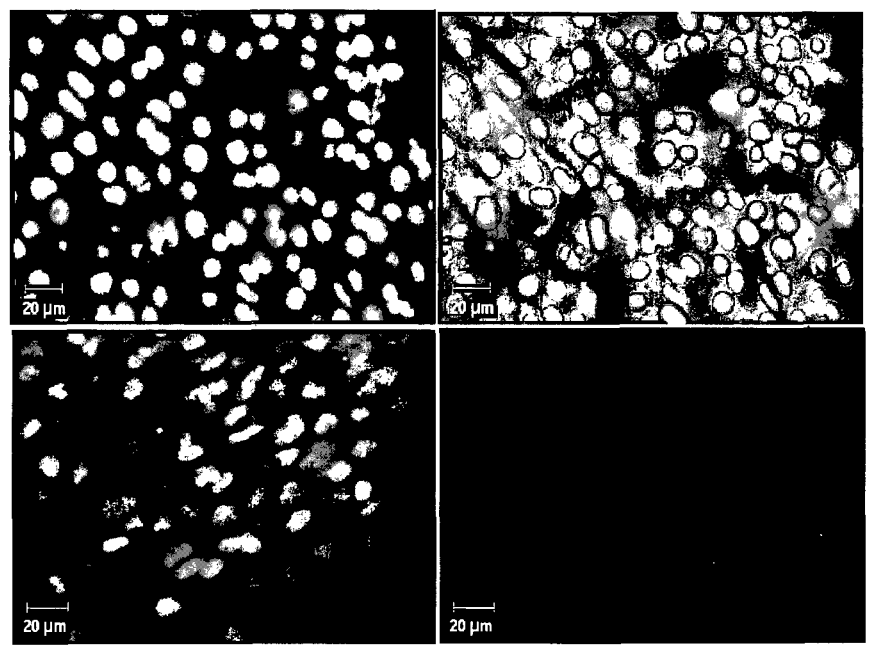
FIG. 7. shows that peptide-treated HES-3 exhibit characteristics of apoptosis. (A) HES-3 pretreated with peptide (top panel) or DMSO (bottom panel) for 24 h were stained using Texas-Red Annexin V and cell-permeable fluorogenic caspase-3 substrate. Scale bar corresponds to 20 µm. (B) Population of peptide-treated HES-3 cells expressing elevated caspase-3 activity. (C) Extent of DNA fragmentation measured by TUNEL using flow cytometry. Error bars represent standard deviation from three determinations indicates significant difference over control ($p<0.01$).
Figure 7B:
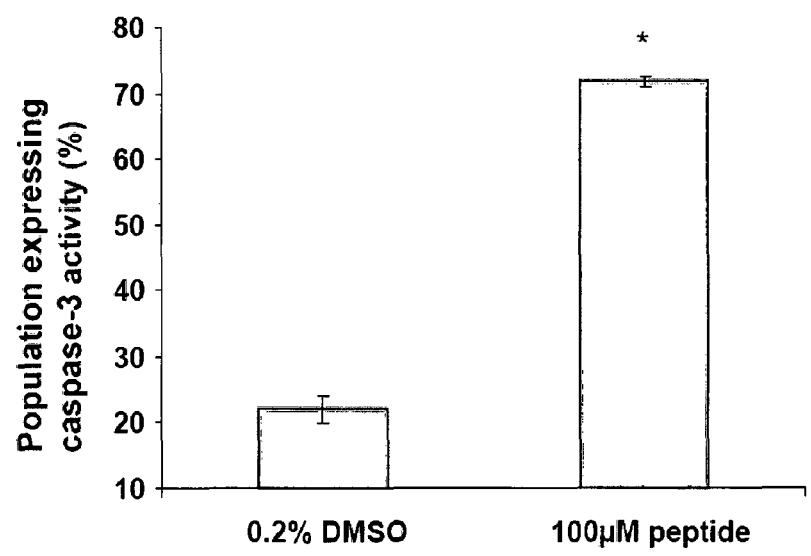
Figure 7C:
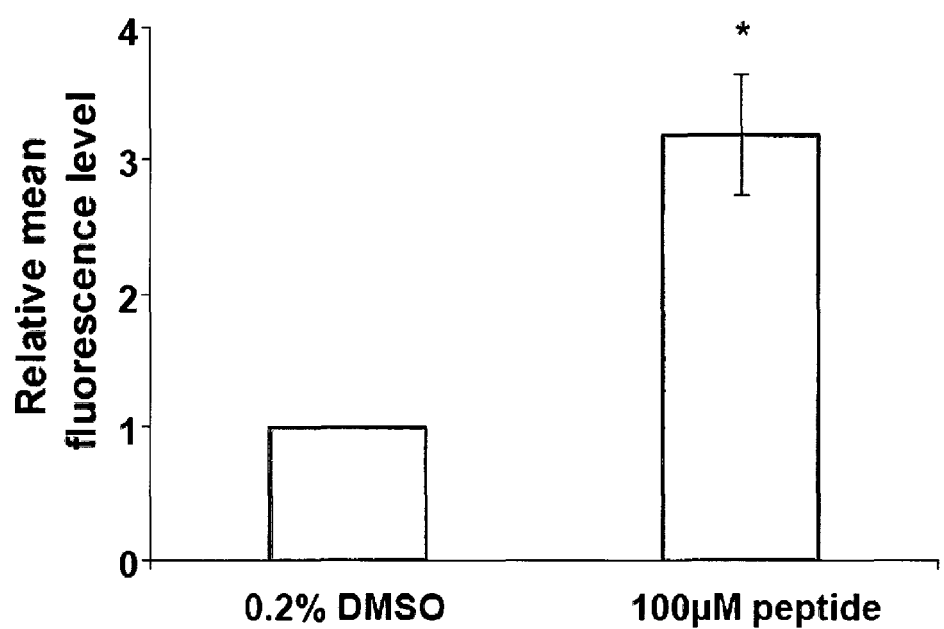
Figure 11B:
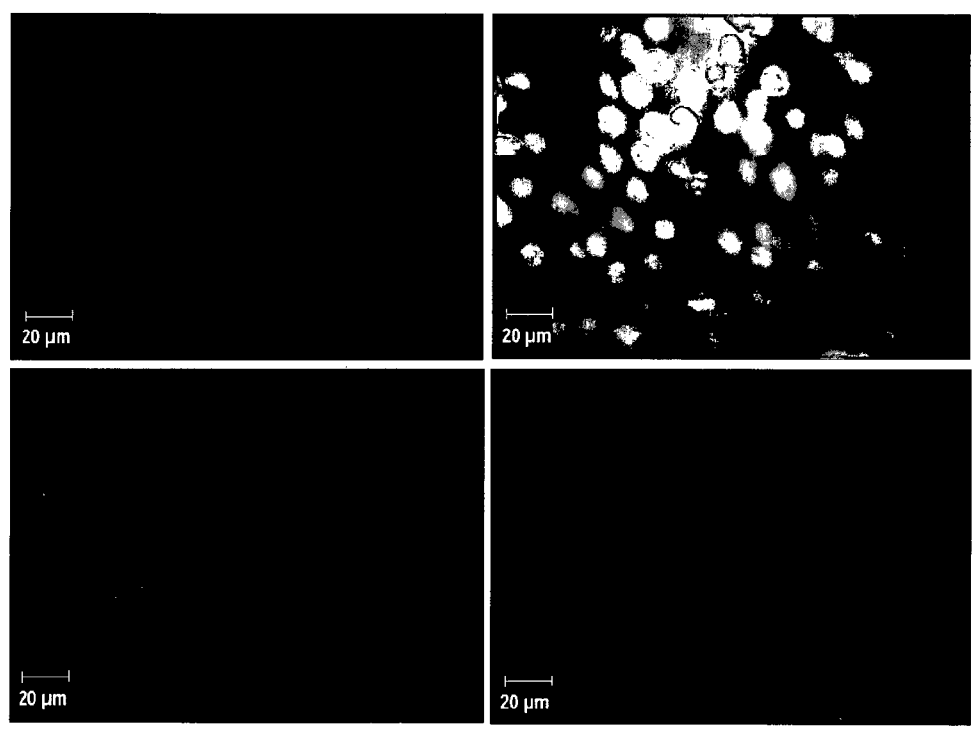
Figure 11C:
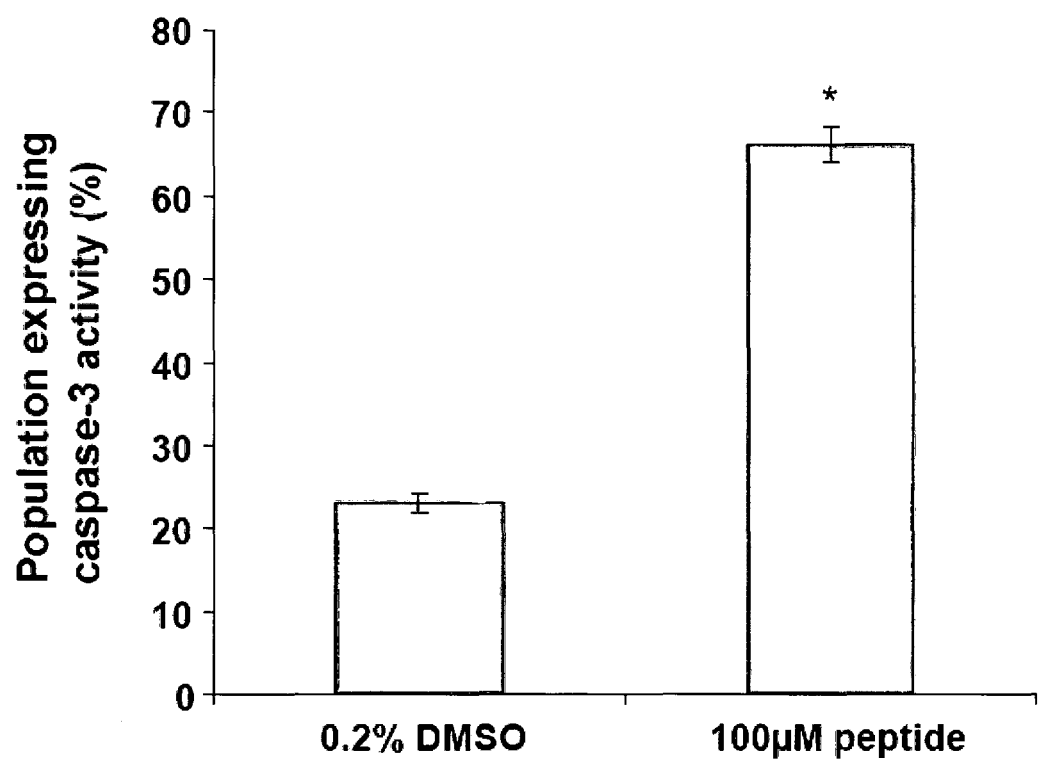

To investigate the mechanism responsible for cell death, we perform biochemical assays to detect for caspase-3 activity and DNA fragmentation. hESC and ESIMR90 cells treated with either 100 μM peptide or 0.2% DMSO for 24 hours were stained with Texas Red Annexin V and a cell-permeable fluorogenic caspase-3 substrate, which labels the cell nuclei green in the presence of caspase-3 activity. As shown in FIG. 7A and FIG. 11B (top panel), peptide-treated hESC and ESIMR90 cells exhibited caspase-3 activity and phosphatidylserine (PS) externalization, which are hallmarks of apoptosis (19-21). In contrast, their control cells remained unstained (FIG. 7A and FIG. 11B, bottom panel). By flow cytometry analysis, 71.1% and 66.3% of the peptide-treated hESC and ESIMR90 population exhibit elevated caspase-3 activity respectively. (FIG. 7B and FIG. 11C). Furthermore, peptide-treated hESC exhibited a significant increase in DNA fragmentation compared to the control after 48 hours via TUNEL assay (FIG. 7C). These results confirm that the peptide is inducing hESC death via apoptosis.

Effect of Dosage on Apoptotic Killing of hESC

Figure 12:
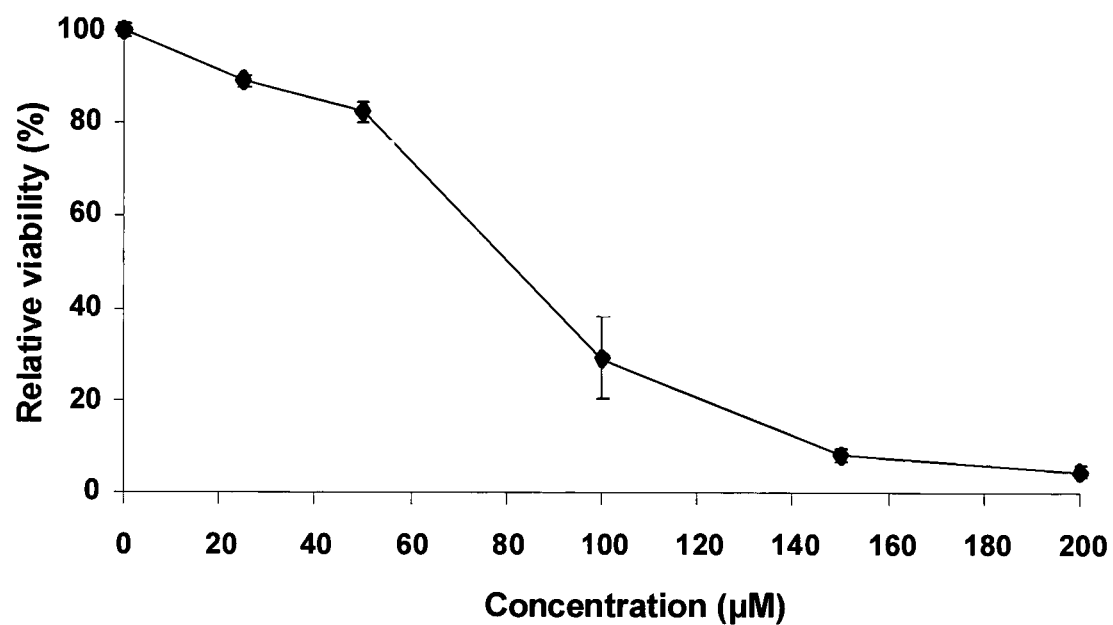
FIG. 12 shows the effect of dosage on apoptotic killing of hESC. The graph shows the relative viability of peptide-treated HES-3 cells at different concentrations after 120 hr. Relative viability (%) was calculated as ratio of the viability of peptide-treated cells to the viability of control cells. Error bars represent standard deviation from three determinations.

When the concentration of peptide was titrated over the range of 20 µM to 200 µM, the apoptotic killing effect on hESC was found to be concentration-dependent (FIG. 12). Significant reduction in viability was only observed at concentrations of 100 µM or more, where the relative viability of peptide-treated hESC cultures dropped to about 30% or less after 120 hr. Viability of hESC cultures were further reduced to <10% at peptide concentrations of 150 µM and 200 µM. However, toxic effect on hESC was minimal at concentrations less than 100 µM.

Effect of Chirality on Apoptotic Killing of hESC

Figure 13:
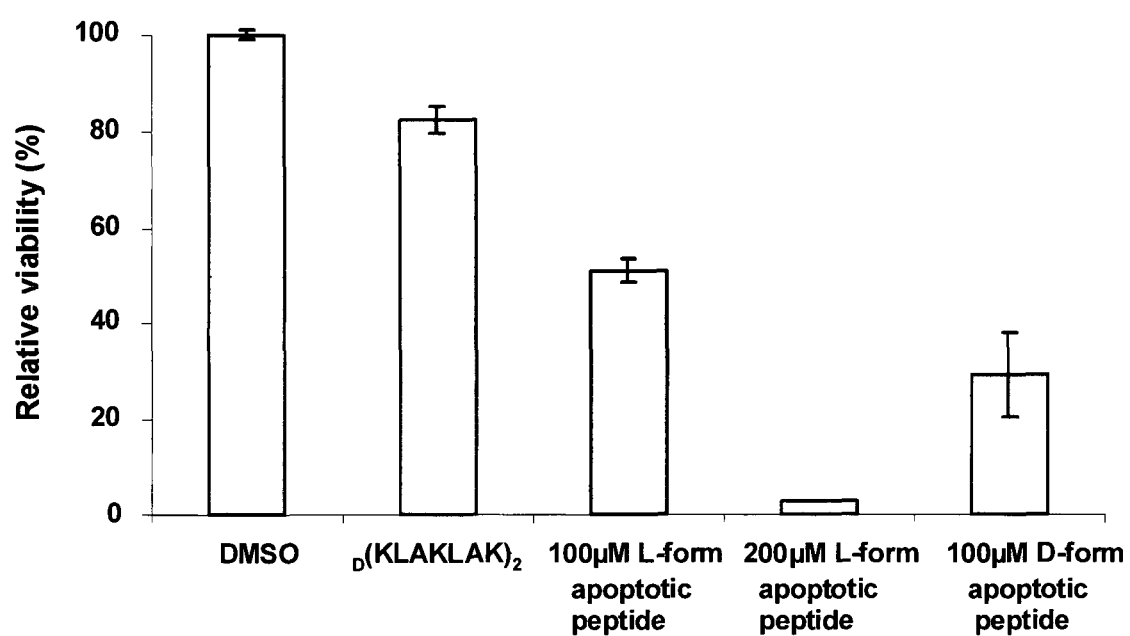
FIG. 13 shows the relationship between chirality of apoptotic peptide and hESC killing efficiency. The graph shows the relative viability of HES-3 cells treated with peptide carrying D and L forms of the proapoptotic motif (KLAKLAK)$_2$ after 120 hr.

The pro-apoptotic peptide used in the study by Kolonin et al carries the apoptotic-inducing motif in D-form due to its resistance to protease degradation, however, since membrane disruption is chiral independent, we hypothesized that the cell killing ability is retained for L-enantiomers. From FIG. 13, it is apparent that killing efficiency of D-form peptide at 100 µm on hESC was comparable to that of L-form peptide. Doubling the concentration of L-form peptide significantly lowers the hESC viability to <5%. These results demonstrate that the ability of the peptide to induce hESC killing is independent of its chirality.

Discussion

Identification of novel hESC surface antigens is essential for characterizing pluripotency and defining developmental stages of differentiation. To achieve this, we previously generated a panel of mAbs which are unique to undifferentiated hESC and do not bind to its differentiated phenotypes (5). In this study, we identified the antigen target for two such mAbs (mAb 375 and mAb 529) as PHB. From immunostaining and flow cytometry analysis, we have shown expression of PHB on the surface of pluripotent hESC, while under differentiating conditions, PHB surface expression is lost. However, PHB was detected in the nucleus of hESC-derived embryoid bodies instead, which may possibly imply a change in functional role under differentiating conditions. Taken together, these data clearly indicates PHB as a surface marker on pluripotent hESC.

PHB is a highly conserved protein with a molecular weight of 30-32 kDa and it belongs to a superfamily of molecules including stomatin, flotillin, which shares a structurally related domain essential for membrane association (12,22). Functionally, PHB has been reported to be involved in diverse cellular processes, depending on its localization. In the mitochondria, it acts as a chaperone protein which stabilizes newly synthesized subunits of mitochondrial respiratory enzymes (6,7). However, in the nucleus, it functions as a cell cycle regulating protein by modulating E2F transcriptional activity (10,15,16). PHB mediates E2F repression by interacting with several other cofactors such as Rb and Brg1 and it is interesting to note that activation of Raf-1 kinase reverses PHB-mediated repression of E2F in human B cells (16). More recently, PHB has been implicated to play a vital role in MAPK pathway, where it is required for recruiting Raf-1 to the membrane for Ras activation (13). This study also describes down-regulation of activated Raf-1 and ERK in the absence of PHB, indicating that MAPK activation is PHB-dependent. Since pluripotent hESC exhibits high levels of MAPK activity (23,24), it led us to hypothesize that PHB on hESC surface helps to maintain high level of MAPK activity by facilitating Raf activation. In our study, preliminary results seem to suggest a dependency between MAPK activation and PHB in hESC as we observe a decline in PHB surface expression as the activation level of MAPK is lowered. Moreover, upon differentiation, when MAPK activation is significantly compromised (23), we failed to detect PHB on membrane as it localizes predominantly in the nucleus instead. Taken together, these results could indicate that PHB surface expression in hESC may be MAPK-dependent.

In a recent report by Kolonin et al (11), they identified the peptide motif, CKGGRAKDC (SEQ ID NO: 1), which binds to PHB expressed in the vasculature of white adipose tissue. By coupling a pro-apoptotic sequence, (KLAKLAK)$_2$ (SEQ ID NO: 2) to this PHB ligand, they were able to target the endothelial cells specifically, which resulted in vascular destruction and ablation of white fat. Since we have identified PHB as a surface marker on undifferentiated hESC, we are interested in assessing the applicability of the peptide, CKGGRAKDC-GG-(KLAKLAK)$_2$ (SEQ ID NO: 3), for eliminating residual undifferentiated hESC after differentiation. In our study, we have demonstrated the efficacy of the peptide to reduce the growth rate and viability of hESC significantly. Furthermore, minimal cell killing effect was observed in IMR-90 cells, which do not express PHB on its membrane, suggesting the specificity of the peptide. Additionally, elevated levels of caspase-3 activity, externalization of PS and an increase in DNA fragmentation in peptide-treated hESC cultures were observed, all of which are hallmark indications of apoptosis (19-21). These data are comparable with the findings in a study by Ellerby et al (25), which revealed similar characteristics when angiogenic endothelial cells were treated with a peptide containing (KLAKLAK)$_2$ pro-apoptotic domain. Furthermore, their report also describes internalization of the peptide into cytosol as being an essential step for inducing cell death. Thus, membrane-associated PHB could likely function as an internalization receptor in hESC, carrying ligands from the extracellular space to the cytoplasm of the cell.

In summary, we have established PHB as a novel surface marker to identify undifferentiated hESC. With this, we went on to validate the use of a pro-apoptotic peptide targeting PHB to selectively bind and kill PHB-expressing hESC. This can potentially be used to eliminate tumorigenic hESC prior to transplantation of hESC-derived progenitor cells. A direct effect of MAPK activation on PHB surface expression in hESC was also observed, suggesting a possible role of PHB in MAPK signaling. However, further investigation needs to be done to fully understand the role of PHB in MAPK pathway.

REFERENCES

1. Reubinoff B E, Pera M F, Fong C Y et al. Embryonic stem cell lines from human blastocysts: somatic differentiation in vitro. Nat. Biotechnol. 2000; 18:399-404.
2. Thomson J A, Itskovitz-Eldor J, Shapiro S S et al. Embryonic stem cell lines derived from human blastocysts. Science 1998; 282:1145-1147.
3. Badcock G, Pigott C, Goepel J et al. The Human Embryonal Carcinoma Marker Antigen TRA-1-60 Is a Sialylated Keratan Sulfate Proteoglycan. Cancer Res 1999; 59:4715-4719.
4. Kannagi R, Cochran N A, Ishigami F et al. Stage-specific embryonic antigens (SSEA-3 and -4) are epitopes of a unique globo-series ganglioside isolated from human teratocarcinoma cells. EMBO J 1983; 2:2355-2361.

5. Choo A B, Tan H L, Ang S N et al. Selection against undifferentiated human embryonic stem cells by a cytotoxic antibody recognizing podocalyxin-like protein-1. Stem Cells 2008; 26:1454-1463.
6. Nijtmans L G, Artal S M, Grivell L A et al. The mitochondrial PHB complex: roles in mitochondrial respiratory complex assembly, ageing and degenerative disease. Cell Mol. Life Sci. 2002; 59:143-155.
7. Nijtmans L G J, de Jong L, Artal Sanz M et al. Prohibitins act as a membrane-bound chaperone for the stabilization of mitochondrial proteins. EMBO J 2000; 19:2444-2451
8. Gamble S C, Chotai D, Odontiadis M et al. Prohibitin, a protein downregulated by androgens, represses androgen receptor activity. Oncogene 2006; 26:1757-1768.
9. Peng X, Mehta R, Wang S et al. Prohibitin is a novel target gene of vitamin D involved in its antiproliferative action in breast cancer cells. Cancer Res 2006; 66:7361-7369.
10. Wang S, Nath N, Adlam M et al. Prohibitin, a potential tumor suppressor, interacts with RB and regulates E2F function. Oncogene 1999; 18:3501-3510.
11. Kolonin M G, Saha P K, Chan L et al. Reversal of obesity by targeted ablation of adipose tissue. Nat. Med. 2004; 10:625-632.
12. Mishra S, Murphy L C, Nyomba B L G et al. Prohibitin: a potential target for new therapeutics. Trends in Molecular Medicine 2005; 11:192-197.
13. Rajalingam K, Wunder C, Brinkmann V et al. Prohibitin is required for Ras-induced Raf-MEK-ERK activation and epithelial cell migration. Nat. Cell Biol. 2005; 7:837-843.
14. Dart D A, Spencer-Dene B, Gamble S et al. Manipulating prohibitin levels provides evidence for an in vivo role in androgen regulation of prostate tumours. Endocr. Relat Cancer 2009.
15. Wang S, Zhang B, Faller D V. Prohibitin requires Brg-1 and Brm for the repression of E2F and cell growth. EMBO J 2002; 21:3019-3028.
16. Wang S, Nath N, Fusaro G et al. Rb and Prohibitin Target Distinct Regions of E2F1 for Repression and Respond to Different Upstream Signals. Mol. Cell. Biol. 1999; 19:7447-7460.
17. Downward J. Targeting RAS signalling pathways in cancer therapy. Nat. Rev. Cancer 2003; 3:11-22.
18. Yu J, Vodyanik M A, Smuga-Otto K et al. Induced pluripotent stem cell lines derived from human somatic cells. Science 2007; 318:1917-1920.
19. Hockenbery D. Defining apoptosis. Am. J. Pathol. 1995; 146:16-19.
20. Majno G, Joris I. Apoptosis, oncosis, and necrosis. An overview of cell death. Am. J Pathol. 1995; 146:3-15.
21. Van Cruchten S, Van Den B W. Morphological and biochemical aspects of apoptosis, oncosis and necrosis. Anat. Histol. Embryol. 2002; 31:214-223.
22. Mishra S, Murphy L C, Murphy L J. The Prohibitins: emerging roles in diverse functions. J Cell Mol. Med. 2006; 10:353-363.
23. Armstrong L, Hughes O, Yung S et al. The role of PI3K/AKT, MAPK/ERK and NFkappabeta signalling in the maintenance of human embryonic stem cell pluripotency and viability highlighted by transcriptional profiling and functional analysis. Hum. Mol. Genet. 2006; 15:1894-1913.
24. Li J, Wang G, Wang C et al. MEK/ERK signaling contributes to the maintenance of human embryonic stem cell self-renewal. Differentiation 2007; 75:299-307.
25. Ellerby H M, Arap W, Ellerby L M et al. Anti-cancer activity of targeted pro-apoptotic peptides. Nat. Med. 1999; 5:1032-1038.

The invention claimed is:

1. A method of isolating a human or mouse embryonic stem (ES) cells or induced pluripotent stem (iPS) cells in a heterogeneous sample containing human or mouse ES cells or iPS cells and cells that have undergone or are undergoing differentiation from human or mouse pluripotent ES cells or iPS cells, comprising:
    (a) obtaining a heterogeneous sample containing human or mouse ES cells or iPS cells and cells that have undergone or are undergoing differentiation from human or mouse pluripotent ES cells or iPS cells,
    (b) contacting the heterogeneous sample of step (a) with an antibody which binds prohibitin (PHB),
    (c) identifying ES iPS cells in the sample of step (b) which are bound to the PHB antibody; and
    (d) isolating the ES or iPS cells from step (c) that express PHB on their cell surface.

2. A method of enriching a human or mouse embryonic stem (ES) cells or induced pluripotent stem (iPS) cells in a heterogeneous sample containing human or mouse ES cells or iPS cells and cells that have undergone or are undergoing differentiation from human or mouse pluripotent ES cells or iPS cells, comprising:
    (a) obtaining a heterogeneous sample containing human or mouse ES cells or iPS cells and cells that have undergone or are undergoing differentiation from human or mouse pluripotent ES cells or iPS cells,
    (b) contacting the heterogeneous sample of step (a) with an antibody which binds prohibitin (PHB),
    (c) identifying ES iPS cells in the sample of step (b) which are bound to the PHB antibody; and
    (d) enriching the ES or iPS cells from step (c) that express PHB on their cell surface.

3. A method of destroying human or mouse ES or iPS cells in a heterogeneous sample containing human or mouse ES or iPS cells and cells that have undergone or are undergoing differentiation from human or mouse ES or iPS cells, comprising:
    (a) obtaining a heterogeneous sample containing human or mouse pluripotent ES or iPS and cells that have undergone or are undergoing differentiation from human or mouse ES or iPS cells,
    (b) contacting the heterogeneous sample of step (a) with a PHB targeting pro-apoptotic peptide comprising the amino acid sequence set forth in SEQ ID NO: 3, and
    (c) destroying the PHB-expressing human or mouse pluripotent ES or iPS cells in the sample of step (b).

* * * * *